US005446024A

United States Patent [19]
Builder et al.

[11] Patent Number: 5,446,024
[45] Date of Patent: Aug. 29, 1995

[54] PURIFICATION OF INSULIN-LIKE GROWTH FACTOR

[75] Inventors: Stuart E. Builder, Belmont; John R. Ogez, Redwood City; Charles V. Olson, Pacifica; David Reifsnyder, San Mateo, all of Calif.

[73] Assignee: Genentech, Inc., South San Francisco, Calif.

[21] Appl. No.: 169,688

[22] Filed: Dec. 17, 1993

[51] Int. Cl.⁶ .................... A61K 38/08; C12N 15/18; C07K 14/00
[52] U.S. Cl. ..................................... 514/12; 530/407; 530/303; 530/399
[58] Field of Search ............... 514/12; 530/407, 303, 530/399

[56] References Cited

U.S. PATENT DOCUMENTS

| | | |
|---|---|---|
| 4,565,785 | 1/1986 | Gilbert et al. . |
| 4,673,641 | 6/1987 | George et al. . |
| 4,710,473 | 12/1987 | Morris . |
| 4,738,921 | 4/1988 | Belagaje et al. . |
| 4,782,139 | 11/1988 | Di Marchi et al. ................. 530/407 |
| 4,795,706 | 1/1989 | Hsiung et al. . |
| 4,988,675 | 1/1991 | Froesch et al. ........................... 514/4 |
| 5,231,178 | 7/1993 | Holz et al. ........................... 530/399 |

OTHER PUBLICATIONS

Bayne et al., "Expression, purification and characterization of recombinant human insulin–like growth factor I in yeast", *Gene*, 66:235–244 (1988).

Builder et al., "Analytical and Process Chromatography in Pharmaceutical Protein Production", *Chemical Engineering Progress*, 84(8):42–46 (1988).

Büttner et al., "Anomalous reversed–phase high–performance liquid chromatographic behavior of synthetic peptides related to antigenic helper T cell sites", *Journal of Chromatography*, 625:191–198 (1992).

Canalis et al., "Isolation and Characterization of Insulin-Like Growth Factor I (Somatomedin–C) from Cultures of Fetal Rat Calvariae*", *Endocrinology*, 122(1):22–27 (1988).

Cohen et al., "Mobile–Phase and Temperature Effects in the Reversed Phase Chromatographic Separation of Proteins", *Analytical Biochemistry*, 140:223–235 (1984).

Coombs, James, *Dictionary of Biotechnology*, 2nd Ed.:96 (1992).

DiMarchi et al., "Utilization of Analytical Reversed–Phase HPLC in Biosynthetic Insulin Production", *High Performance Liquid Chromatography in Biotechnology*, 8:181–189 (1990).

DiMarchi et al., "Synthesis of Insulin–Like Growth Factor I Through Recombinant DNA Techniques and Selective Chemical Cleavage at Tryptophan", *Synthetic Peptides: Approaches to Biological Problems*, pp. 283–294 (1989).

Elliott et al., "Yeast–Derived Recombinant Human Insulin–Like Growth Factor I: Production, and Structural Characterization", *Journal of Protein Chemistry*, 9(1):95–104 (1990).

Fink et al., "Characterization of the Unfolding of Ribonuclease A in Aqueous Methanol Solvents", *Biochemistry*, 26:1665–1671 (1987).

Forsberg et al., "Comparison of two chemical cleavage methods for preparation of a truncated form of recombinant human insulin–like growth factor I from a secreted fusion protein", *BioFactors*, 2(2):105–112 (1989).

Francis et al., "Purification and partial sequence analysis of insulin–like growth factor–1 from bovine colostrum", *Biochem J.*, 233:207–213 (1986).

(List continued on next page.)

*Primary Examiner*—Howard E. Schain
*Assistant Examiner*—Lynn Touzeau
*Attorney, Agent, or Firm*—Janet E. Hasak

[57] ABSTRACT

A process for purifying IGF-I from variants of IGF-I is provided. In this process a mixture containing IGF-I and its variants is loaded onto a reversed-phase liquid chromatography column and the IGF-I is eluted from the column with a buffer at a pH of about 6–8. The buffer contains an alcoholic or polar aprotic solvent at a concentration of about 20–30% (v/v). This process can be preceded by a hydrophobic-interaction chromatography step.

19 Claims, 18 Drawing Sheets

OTHER PUBLICATIONS

Frenz et al., "Reversed Phase Chromatography in Analytical Biotechnology of Proteins", *HPLC of Biological Macromolecules*, (6):145–177 (1990).

Furlanetto et al., "Estimation of Somatomedin-C Levels in Normals and Patients with Pituitary Disease by Radioimmunoassay", *Journal of Clinical Investigation*, 60:648:657 (1977).

Gospodarowicz et al., "Isolation of Pituitary Fibroblast Growth Factor by Fast Protein Liquid Chromatography (FPLC): Partial Chemical and Biological Characterization", *Joural of Cellular Physiology*, 122:323–332 (1985).

Horner et al., "Further Comparisons of the [$^{125}$I]-Somatomedin A and the [$^{125}$I]Somatomedin C Radioreceptor Assays of Somatomedin Peptide", *Journal of Clinical Endocrinology and Metabolism*, 48(6):959–963.

Hummel et al., "Gene synthesis, expression in *Escherichia coli* and purification of immunoreactive human insulin-like growth factors I and II", *Eur. J. Biochem.*, 180:555–561 (1989).

Jabri et al., "Adverse Effects of Recombinant Human Insulin-Like Growth Factor I in Obese Insulin-Resistant Type II Diabetic Patients", *Diabetes*, 43:369–374 (1994).

Kerr et al., "Effect of Insulin-like Growth Factor-1 on the Responses to and Recognition of Hypoglycemia in Humans", *J. Clin. Invest.*, 91:141–147 (1993).

King et al., "Production and characterization of recombinant insulin-like growth factor-I (IGFD-I) and potent analogues of IGF-I, with Gly or Arg substituted for Glu$^3$, following their expression in *Escherichia coli* as fusion proteins", *J. Molecular Endocrinology*, 8:29–41 (1992).

Kolaczynski et al., "Insulin-like Growth Factor-1 Therapy in Diabetes: Physiologic Basis, Clinical Benefits, and Risks", *Annals of Internal Medicine*, 120(1):47–55 (1994).

Kuzuya et al., "Trial of Insulinlike Growth Factor I Therapy for Patients With Extreme Insulin Resistance Syndromes", *Diabetes*(42):696–705 (1993).

Lau et al., "Effects of High-Performance Liquid Chromatographic Solvents and Hydrophobic Matrices on the Secondary and Quaternary Structure of a Model Protein", *Journal of Chromatography*, 317:129–140 (1984).

Mahoney et al., "Separation of Large Denatured Peptides by Reverse Phase High Performance Liquid Chromatography", *Journal of Biological Chemistry*, 255(23):11199–11203 (1980).

McKinnon et al., "Expression, purification and characterization of secreted recombinant human insulin-like growth factor-I (IGF-I) and the potent variant des(-1–3)IGF-I in Chinese hamster ovary cells", *Journal of Molecular Endocrinology*, 6:231–239 (1991).

Monger et al., "Reversed-phase chromatographic behaviour of β-endorphin: evidence of conformational change", *Journal of Chromatography*, 595:125–135 (1992).

Morrell et al., "Somatomedin C/insulin-like growth factor I: simplified purification procedure and biological activities of the purified growth factor", *J. Endocr.*, 110:151–158 (1986).

Oroszlan et al., "Conformational Effects in the Reversed-Phase Chromatographic Behavior of Recombinant Human Growth Hormone (rhGH) and n-Methionyl Recombinant Human Growth Hormone (Met-hGH)", *Anal. Chem.*, 64:1623–1631 (1992).

Regnier, Fred E., "High-Performance Liquid Chromatography of Proteins", *Methods in Enzymology*, 91:137, 180–190 (1983).

Riggin et al., "A Reversed-Phase High-Performance Liquid Chromatographic Method for Characterization of Biosynthetic Human Growth Hormone", *Analytical Biochemistry*, 167:199–209 (1987).

Sadler et al., "Protein Conformation and Reversed-Phase High-Performance Liquid Chromatography", *J of Chromatography*, 317:93–101 (1984).

Saito et al., "Production and Isolation of Recombinant Somatomedin C", *J. Biochem.*, 101:123–134 (1987).

Schalch et al., "Short-term Effects of Recombinant Human Insulin-Like Growth Factor I on Metabolic Control of Patients with Type II Diabetes Mellitus", *J. of Clinical Endo. and Metabolism*, 77(6):15631568 (1993).

Schoenle et al., "Recombinant human insulin-like growth factor I (rhIGF I) reduces hyperglycaemia in patients with extreme insulin resistance", *Diabetologia*, 34:675–679 (1991).

Schweitzer, Philip A., "Handbook of Separation Tech-

OTHER PUBLICATIONS niques for Chemical Engineers", *2nd Edi.*(2):101–103 (1988).

Straczek et al., "Purification and Characterization of Three Molecular Forms of Somatomedins/Insulin–Like Growth Factors From Human Cohn Paste IV", *Biotechnology of plasma proteins; Colloque INSERM*, 175:115–122 (1989).

Usala et al., "Brief Report: Treatment of Insulin–Resistant Diabetic Ketoacidosis With Insulin–Like Growth Factor I In An Adolescent With Insulin–Dependent Diabetes", *The New England Journal of Medicine Brief Report*, 327(12):853–857 (1992).

Van den Brande et al., "Isolation and partial characterization of IGF–like peptides from Cohn fraction IV of human plasma", *Acta Endocrinologica*, 122:683–695 (1990).

Wadensten et al., "Purification of Human Recombinant Insulin–Like Growth Factors (IGF:s) Using Kromasil® Reverse Phase Columns", *KG—KabiGen, EN–Eka Nobel Industries Sweden*, pp. 1–15.

Watson et al., "Multiple peak formation from reversed–phase liquid chromatography of recombinant human platelet–derived growth factor", *J. of Chromatography*, 606:165–170 (1992).

Welinder et al., "Bioactivity of Insulin and Iodinated Insulin after Reversed–Phase HPLC", *High Performance Liquid Chromatography in Biotechnology*, 4:79–90 (1984).

Welinder et al., "Reversed–Phase High–Performance Liquid Chromatographic Separation of the Four Monoiodoinsulins: Effect of Column Supports, Buffers and Organic Modifiers", *Journal of Chromatography*, 298:41–57 (1984).

Welinder et al., "Reversed–Phase High–Performance Liquid Chromatography of Insulin and Insulin Derivatives–A Comparative Study", *J. of Chromatography*, 348:347–361 (1985).

Wilson et al., "Comparison of the High–Performance Liquid Chromatography of Peptides and Proteins on 100– and 300–A Reversed–Phase Supports", *J. of Chromatography*, 237:407–416 (1982).

Wilson et al., "Somatomedins in Pregnancy: A Cross–Sectional Study of Insulin–Like Growth Factors I and II and Somatomedin Peptide Content in Normal Human Pregnancies", *J. of Clinical Endocrinology and Metabolism*, 55(5):858–861 (1982).

Zenobi et al., "Insulin–like Growth Factor–I Improves Glucose and Lipid Metabolism in Type 2 Diabetes Mellitus", *J. Clin. Invest.*, 90:2234–2241 (1992).

"Insulin–like growth factor I (IGF-1) for growth hormone insensitivty in Sweden", *Scrip*, 1938:24 (1994).

"Launch of Igef in Sweden", *Scrip*, 1939:23 (1994).

Francis et al, "Insulin–like growth factors I and II in Bovine Colostrum," *Biochem J*. 251, 95–103 (1988).

Baxter, "The Somatomedins: Insulin–Like Growth Factors", *Adv. Clin. Chem.*, 25:491 ∝ 115, (1986).

Binoux, "Donnees recentes sur les somatomedines (Insulin–like growth Factors)", *Ann, Endocrinol.*, 41:157–192, (1980).

Canova–Davis et al., "Chemical heterogeneity as a result of hydroxylamine cleavage of a fusion protein of human insulin–like growth factor I", *Biochem. J.*, 285:207–213, (1992).

Clemmons et al., "Somatomedin: Physiological Control and Effects on Cell Proliferation", *Handbook Exp. Pharmacol.* 7:161–208, (1981).

Cornell et al., "Isolation of Insulin–Like Growth Factors I and II from Human Plasma", *Prep. Biochem.*, 14(2):123–138, (1984).

Cornell et al., "Application of Preparative Reversed–Phase High Performance Liquid Chromatography to the Isolation of Insulin–Like Growth Factor II from Human Serum", *J. Chromatography*, 421:61–69, (1987).

Forsberg et al., "Separation and characterization of modified variants of recombinant human insulin–like growth factor I derived from a fusion protein secreted from *Escherichia coli*", *Biochem. J.*, 271:357–363, (1990).

Francis et al., "Sheep Insulin–Like Growth Factors I and II: Sequences, Activities and Assays", *Endocrinology*, 124:1173–1183, (1989).

Gabriel, "Simple, rapid method for converting a peptide from one salt form to another", *Int. J. Peptide Protein Res*, 30:40–43, (1987).

Guler et al., "Short–term Metabolic Effects of Recombinant Human INsulin–Like Growth Factor I in Healthy Adults", *N. Eng. J. Med.*, 317, 137–140, (1987).

Guler et al., "Recombinant human insulin–like growth factor I stimulates growth and has distinct effects on organ size in hypophysectomized rats", *Proc. Natl. Acad. Sci.* 85:4889–4893. (1988).

Kroeff et al., "Production Scale Purification of Biosynthetic Human Insulin by Reversed–Phase High-Performance Liquid Chromatography", *J. of Chroma.*, 461:45–61, (1989).

OTHER PUBLICATIONS

Linde et al., "Non-ideal behavior of silica-based stationary phases in trifluoroacetic acid-acetonitrile-based reversed-phase high-performance liquid chromatographic separations of insulin and proinsulins", *J. of Chroma.*, 536:43–55. (1991).

Moks et al., "Large-Scale Affinity Purification of Human Insulin-Like Growth Factor I from Culture Medium of *Escherichia Coli*", *Bio/Technology*, 5:379–382, (1987).

Nice et al., "Comparison of Short and Ultrashort-Chain Alkylsilane-Bonded Silicas for the High-Performance Liquid Chromatography of Proteins by Hydrophobic Interaction Methods", *J. of Chroma.*, 218:569–580, (1981).

O'Hare et al., "Hydrophobic High Performance Liquid Chromatography of Hormonal Polypeptides and Proteins on Alkylsilane-Bonded Silica", *J. of Chroma.*, 171:209–226, (1979).

Petrides et al., "An Improved Method for the Purification of Human Insulin-Like Growth Factors I and II", *Endocrinology*, 118:2034–2038 (1986).

Raschdorf et al., "Location of Disulphide Bonds in Human Insulin-Like Growth Factors (IFGs Synthesized by Recombinant DNA Technology", *Biomed. and Environ. Mass Spec.*, 16:3–8, (1988).

Rinderknecht et al., "The Amino Acid Sequence of Human Insulin-like Growth Factor I and Its Structural Homology with Proinsulin", *J. of Bio. Chem.*, 253(8):2769–2776, (1978).

Rinderknecht et al., "Polypeptides with nonsuppressible insulin-like and cell-growth promoting activities in human serum: Isolation, chemical characterization, and some biological properties of forms I and II", *Proc. Natl. Acad. Sci.*, 73(7):2365–2369 (1976).

Sofer, "Current Application in Chromatography in Biotechnology", *Bio/Technology*, 4:712–715, (1986).

Svoboda et al., "Purification of Somatomedin-C from Human Plasma: Chemical and Biological Properties, Partial Sequence Analysis, and Relationship to Other Somatomedins", *Biochemistry*, 19:790–797, (1980).

Underwood et al., "Regulation of Somatomedin-C/Insulin-Like Growth Factor I by Nutrients", *Hormone Res.*, 24:166–176, (1986).

Van Wyk et al., "The Somatomedins: A Family of Insulinlike Hormones under Growth Hormone Control", *Recent Progress Horm. Res.*, 30:259–318, (1974).

FIG. 2

EcoRI (1149)
5'-GAATTCATGAGAGATTCCTTCAATTTTACTGCAGTTTATTCGCAGCATCCTCCGCATTAGC

TGCTCCAGTCAACACTACAACAGAAGATGAAACGGCACAAATTCCGGCTGAAGCTGTCATCGGTT

ACTTAGAGATTTAGAAGGGGATTTCGATGTTGCTGTTTTGCCATTTCCAACAGCACAAATAACGGG

TTATTGTTTATAAATACTACTATTGCCAGCATTGCTGCTAAAGAAGAAGGGGTATCTTTGATAA

HaeII                            PstI
AAGAGGTCCGGAAACTCTGTGCGGGCCTGGTTGACGCTCTGCAGTTCGTATGTGGTGATC

BamHI
GAGGCTTCTACTTCAACAAACCGACTGGGTACGGATCCTCCTCGTCGTCCGCAAACCGGC

ATCGTTGATGAATGCTGTTTTCGGTCCTCTGTGACCTTCGCCGTCTCGAAATGTACTGCGCTCCGCT

SalI     EcoRI (1633)
GAAACCGGCTAAGTCTGCATAGTCGACGAATTC-3'

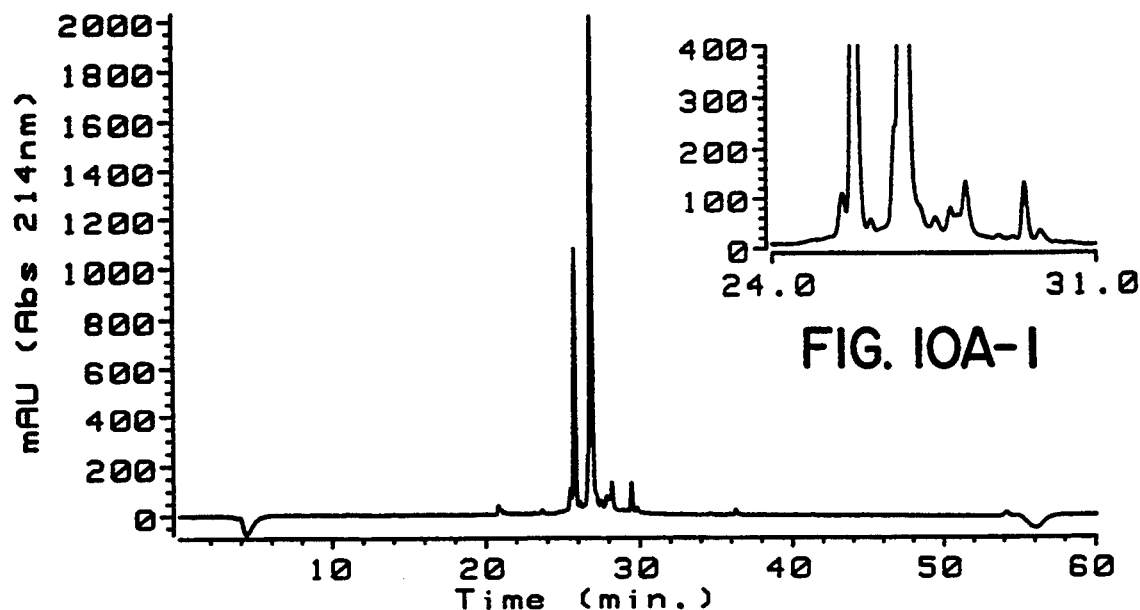
FIG. 10A-1
FIG. 10A
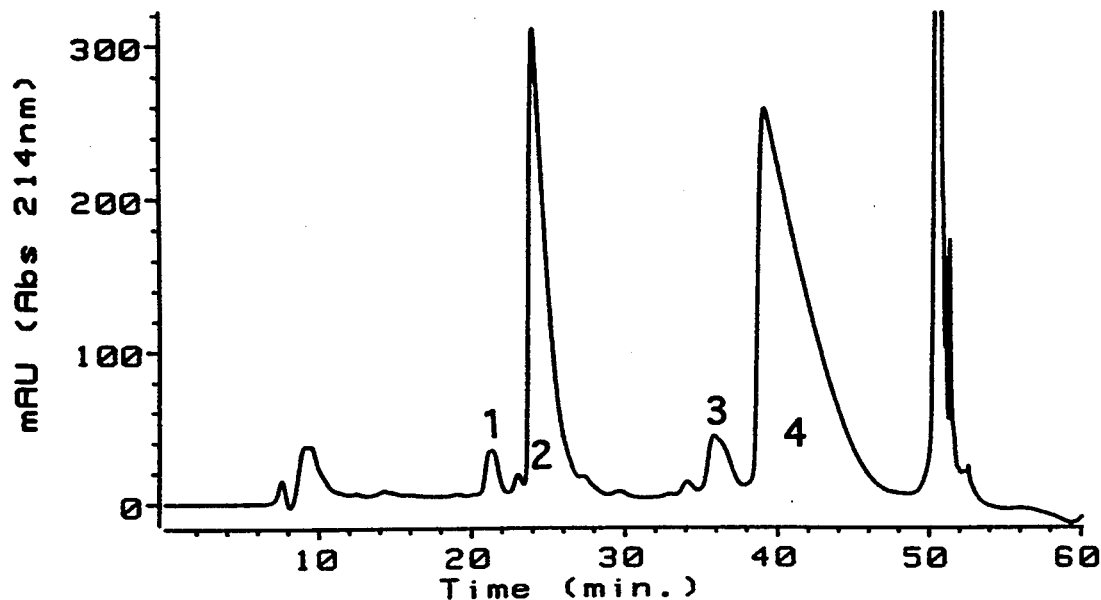
FIG. 10B

PURIFICATION OF INSULIN-LIKE GROWTH FACTOR

BACKGROUND OF THE INVENTION

1. Field of the Invention

This invention relates to an improved method for purifying insulin-like growth factor (IGF-I) from variants, impurities, and contaminants associated therewith, particularly when it is produced by bacterial fermentation.

2. Description of Related Art

The production of large quantities of relatively pure, biologically active polypeptides and proteins is important economically for the manufacture of human and animal pharmaceutical formulations, enzymes, and other specialty chemicals. For production of many proteins, recombinant DNA techniques have become the method of choice because large quantities of exogenous proteins can be expressed in bacteria and other host cells. The expression of proteins by recombinant DNA techniques for the production of cells or cell parts that function as biocatalysts is also an important application.

Human insulin-like growth factor-I (IGF-I) is a 7649-dalton polypeptide with a pI of 8.4 [Rinderknecht and Humbel, *Proc. Natl. Acad. Sci. USA*, 73: 2365 (1976); Rinderknecht and Humbel, *J. Biol. Chem.*, 253: 2769 (1978)] belonging to a family of somatomedins with insulin-like and mitogenic biological activities that modulate the action of growth hormone. Van Wyk et al., *Recent Prog. Horm. Res.*, 30: 259 (1974); Binoux, *Ann. Endocrinol.*, 41: 157 (1980); Clemmons and Van Wyk, *Handbook Exp. Pharmacol.*, 57: 161 (1981); Baxter, *Adv. Clin. Chem.*, 25: 49 (1986). IGF-I has hypoglycemic effects similar to insulin but also promotes positive nitrogen balance. Underwood et al., *Hormone Res.*, 24: 166 (1986); Guler et al., *N. Eng. J. Med.*, 317: 137 (1987). Due to this range of activities, IGF-I is being tested in humans for uses ranging from wound healing to the reversal of whole body catabolic states. Guler et al., *Proc. Natl. Acad. Sci. USA*, 85: 4889 (1988).

Producing recombinant protein involves transfecting host cells with DNA encoding the protein and growing the cells under conditions favoring expression of the recombinant protein. The prokaryote *E. coli* is favored as host because it can be made to produce recombinant proteins in high yields. Numerous U.S. patents on general bacterial expression of DNA encoding proteins exist, including U.S. Pat. No. 4,565,785 on a recombinant DNA molecule comprising a bacterial gene for an extracellular or periplasmic carrier protein and nonbacterial gene; U.S. Pat. No. 4,673,641 on co-production of a foreign polypeptide with an aggregate-forming polypeptide; U.S. Pat. No. 4,738,921 on an expression vector with a trp promoter/operator and trp LE fusion with a polypeptide such as IGF-I; U.S. Pat. No. 4,795,706 on expression control sequences to include with a foreign protein; and U.S. Pat. No. 4,710,473 on specific circular DNA plasmids such as those encoding IGF-I.

Genetically engineered bio-pharmaceuticals are typically purified from a supernatant containing a variety of diverse host cell contaminants. There is a need in the art for an efficient protocol for selectively separating IGF-I from other molecules, particularly other hydrophobic polypeptides, in the process of purifying IGF-I from a fermentation broth, particularly since the final process pool contains several variant species of recombinant, human IGF-I (rhIGF-I) that are difficult to separate.

IGF-I has been purified using gel filtration followed by ion-exchange chromatography on a sulfopropyl-substituted cation-exchange column, followed by buffer exchange and fractionation by a second gel filtration step. Next, preparative isoelectric focusing further separated the IGF-I from contaminants with similar isoelectric points, followed by two reversed-phase chromatography steps to obtain pure IGF-I. Cornell et al., *Prep. Biochem.*, 14: 123 (1984). Clearly, because of the large number of steps involved, this protocol is relatively inefficient.

An alternative protocol for purifying IGF-I requires the fusion of a Protein A fragment to IGF-I by a linker, where the culture supernatant is passed through an affinity column consisting of IgG coupled to agarose. The IGF-I fusion product binds to the column while contaminants pass through and the bound material is eluted, treated to remove the linker, and passed through IgG-agarose to remove the free Protein A. See Moks et al., *Bio/Technology*, 5: 379–382 (1987); Sofer, *Bio/Technology*, 4: 712–715 (1986).

IGF-I has been also purified by a series of adsorption-desorption steps employing a combination of cation-exchange and hydrophobic-interaction adsorbents. See U.S. Pat. No. 5,231,178 issued Jul. 27, 1993. See also KR 9208377 published Sep. 26, 1992 for another method for purifying IGF-I.

Procedures utilizing reversed-phase high performance liquid chromatography (RP-HPLC) have been published for many molecules [Bidlingmeyer, ed., *Preparative Liquid Chromatography* (Elsevier, Amsterdam, 1987)]. Irreversible binding of insulin and proinsulin to C18 stationary phases has recently been reported [Linde and Welinder, *J. Chromatogr.*, 536: 43 (1991)], with the C4 alkyl chain substitution being preferred to maximize product recovery. Nice et al., *J. Chromatogr.*, 218: 569 (1981). Such RP-HPLC procedures are included in the purification of native IGF-I, synthetic IGF-I, and rhIGF-I. Svoboda et al., *Biochemistry*, 19: 790 (1980); Petrides et al., *Endocrinology*, 118: 2034 (1986); Cornell and Brady, *J. Chromatogr.*, 421: 61 (1987); Francis et al., *Endocrinology*, 124: 1173 (1989). However, preparative RP-HPLC isolation of a recombinant protein resulting in pharmaceutical purity and high yield has eluded the art. Kroeff et al., *J. Chromatogr.*, 461: 45 (1989). Furthermore, the typical pH at which such purification step is operated using a mobile phase is an acid pH, generally around pH 2–3 using trifluoroacetic acid.

Accordingly, it is an object of this invention to provide an improved process for separating IGF-I from its related fermentation variants by means of reversed-phase liquid chromatography.

It is another object to provide a process for purifying IGF-I from related variants using elution conditions involving physiological pH.

It is still another object to provide a process for purifying IGF-I that results in considerable improvement in its homogeneity.

These and other objects will be apparent to those of ordinary skill in the art.

SUMMARY OF THE INVENTION

This invention provides, in one aspect, a process for purifying IGF-I from variants of IGF-I comprising loading a mixture containing IGF-I and the variants onto a reversed-phase liquid chromatography column and eluting the IGF-I from the column with a buffer at a pH of about 6–8 containing an alcoholic or polar aprotic solvent at a concentration of about 20–30% (v/v).

In another aspect, the invention provides a process for separating IGF-I from variants thereof comprising:
  (a) loading a buffer containing IGF-I and its variants at a pH of about 3–8 onto a hydrophobic interaction chromatography column;
  (b) washing the column with a buffer at a pH of about 3–8;
  (c) eluting the IGF-I with a buffer at a pH of about 3–8;
  (d) loading the IGF-I-containing eluant onto a reversed-phase liquid chromatography column; and
  (e) eluting the IGF-I from the column with a buffer at a pH of about 6–8 containing an alcoholic or polar aprotic solvent at a concentration of about 20–30% (v/v).

The isolation of recombinant human IGF-I involves separation of the protein from a variety of diverse host cell contaminants. Each step involves special buffers that enable sufficient separation to take place. The final processing step for IGF-I is complicated by the presence of several IGF-I variants that co-purify using conventional chromatographic media. These species consist primarily of a methionine-sulfoxide variant of the properly folded molecule and a misfolded form and its respective methionine sulfoxide variant.

In the present invention solution conditions are identified that are favorable for selectively separating IGF-I from these and other closely related variants. The acidic pH in the range of 2–3 used previously in the RP-HPLC process is replaced with a more neutral, protein friendly pH in the range of about 6–8. Accordingly, the process minimizes the damage to the IGF-I ultimately purified.

BRIEF DESCRIPTION OF THE DRAWINGS

FIG. 2 depicts the nucleotide sequence of the EcoRI-EcoRI fragment (from positions 1149 to 1633) of p200 containing the MF alpha I prepro and IGF-I gene sequences (SEQ. ID NO. 1).

FIG. 10A illustrates a gradient RP-HPLC analysis, wherein chromatography was performed on a 5-μm Vydac-C18 column using a 10–60% acetonitrile (ACN) gradient over 50 minutes, 0.1% trifluoroacetic acid (TFA), 1 mL/minute, 22° C. The process pool sample was diluted five-fold into the initial mobile phase and 250 μL was loaded. The inset (FIG. 10-A1) shows an expanded view of the later eluting peaks. FIG. 10B is an isocratic RP-HPLC analysis, wherein the chromatography was performed isocratically on a 5-μm Vydac-C18 column at 28.5% ACN, 0.1% TFA, 0.5 mL/minute, 50° C. The process pool sample was diluted ten-fold into the mobile phase and 25 μL was loaded. After 40 minutes, the column was washed with 60% ACN to remove the more hydrophobic species. The four predominant rhIGF-I variants are labeled on the chromatogram: (1) methionine-sulfoxide/misfolded, (2) misfolded, (3) methionine sulfoxide, and (4) correctly folded monomer (rhIGF-I).

FIG. 12A is an analytical separation on preparative media, wherein the preparative RP-HPLC chromatography was performed on an analytical size, 0.39×30 cm, 15-μm Waters-C4 column: 27–28% ACN/40 minutes, 20 mM acetic acid, 20 mM NaCl, pH 3, 0.5 mL/minute, 50° C. rhIGF-I (20 μg) was loaded onto the column and four peak fractions were collected. FIG. 12B is an analysis of peak fractions, wherein the rapid analytical chromatography was performed on a 5-μm Vydac-C18 column using a modified version of the initial analysis (FIG. 12B). The flow rate was increased to 2 mL/minute at 50° C. A 28–29% ACN/10 minutes gradient, with 0.1% TFA, maintained a constant gradient volume. The fractions collected from panel A were diluted two-fold with water and 100 μL was injected. The four predominant rhIGF-I species are labeled on the chromatogram: (1) methionine sulfoxide/misfolded (MS-MF), (2) misfolded (MF), (3) methionine sulfoxide (MS), and (4) correctly folded monomer (rhIGF-I). FIG. 12C is effective loading capacity, wherein the chromatography was performed as described for FIG. 12A. Increasing levels of rhIGF-I were sequentially loaded onto the column from 5 to 100 μg rhIGF-I/mL bed volume.

FIG. 13A is 20 mM acetic acid+20 mM NaCl, pH 3, 22° C., 26–27% ACN; FIG. 13B is 20 mM acetic acid+20 mM NaCl, pH 3, 50° C., 27–28% ACN; FIG. 13C is 20 mM Na$_2$HPO$_4$, pH 3, 50° C., 27–28% ACN; FIG. 13D is 20 mM acetic acid+20 mM NaCl, pH 5, 50° C., 26–27% ACN; FIG. 13E is 20 mM Na$_2$HPO$_4$, pH 7, 50° C., 23–24% ACN; and FIG. 13F is 100 mM Na$_2$HPO$_4$, pH 7, 50° C., 23–24% ACN.

FIG. 14A is differential selectivity at pH 7, where the preparative RP-HPLC chromatography was performed on a 15-μm Waters-C4 column using the conditions specified (FIG. 13F), 23–24% ACN/40 minutes, 100 mM Na$_2$HPO$_4$, pH 7, 0.7 mL/minute, 50° C. A mixture of different IGF-I species (100 μg) was loaded onto the column and four peak fractions were collected. FIG. 14B is an analysis confirming the shift in retention times. The rapid analytical chromatography was performed on a 5-μm Vydac-C18 column as in FIG. 12B. The fractions collected from FIG. 14A were diluted two-fold with water and 100 μL was injected. The order of elution of the species was altered as labeled on the chromatogram: (1) methionine-sulfoxide (MS), (2) methionine-sulfoxide/misfolded (MS-MF) and a second rhIGF-I co-eluting peak, (3) rhIGF-I, and (4) misfolded (MF). FIG. 14C shows effective loading capacity. The chromatography was performed as in FIG. 14A. Increasing levels of rhIGF-I were sequentially loaded onto the column from 50 to 1000 μg rhIGF-I/mL bed volume.

FIG. 15A is Waters-C4, 15 μm, 300 Å, 23–24% ACN; FIG. 15B is YMC-C8, 15 μm, 300 Å, 23.5–24.5% ACN; FIG. 15C is Baker-C4, 15 μm, 275 Å, 22.5–23.5% ACN; FIG. 15D is Kromasil-C8, 10 μm, 20 Å, 25–26% ACN; FIG. 15E is IMPAQ-C4, 20 μm, 200 Å, 25–26% ACN; FIG. 15F is Amicon-C8, 20 μm, 250 Å, 26–27% ACN; FIG. 15G is PLRP-S, 8 μm, 300 Å, 23–24% ACN; and FIG. 15H is Eurosil-C4, 7 μm, 300 Å, 21.5–22.5% ACN.

DESCRIPTION OF THE PREFERRED EMBODIMENTS

A. Definitions

Figure 1:
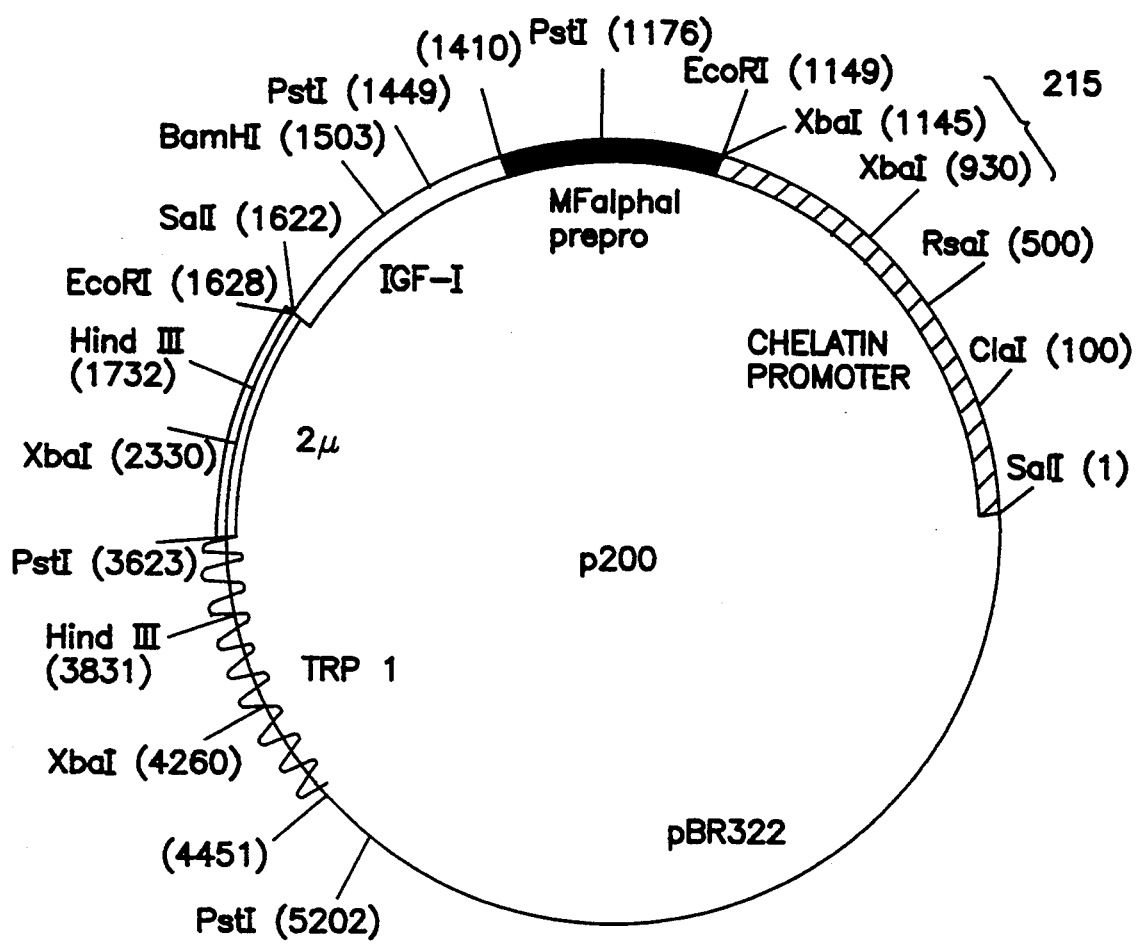
FIG. 1 shows a restriction map for plasmid p200, used to produce pLamBIGF, an intermediate plasmid in the production of pLBIGFTsc, used to prepare pBKIGF-2, an intermediate plasmid in preparing an expression vector encoding IGF-I, namely, pBKIGF-2B.

As used herein, "IGF-I" refers to insulin-like growth factor from any species, including bovine, ovine, porcine, equine, avian, and preferably human, in native sequence or in variant form, and from any source, whether natural, synthetic, or recombinantly produced. Preferably, the IGF-I is recombinantly produced. In a preferred method, the IGF-I is cloned and its DNA expressed, e.g., by the process described in EP 128,733 published Dec. 19, 1984.

Preferred for human use is human native-sequence, mature IGF-I, more preferably without a N-terminal methionine, prepared, e.g., by the process described in EP 230,869 published Aug. 5, 1987; EP 128,733 published Dec. 19, 1984; or EP 288,451 published Oct. 26, 1988. More preferably, this native-sequence IGF-I is recombinantly produced and is available from Genentech, Inc., South San Francisco, Calif. for clinical investigations.

The preferred IGF-I variants are those described in U.S. Pat. No. 5,077,276 issued Dec. 31, 1991, in PCT WO 87/01038 published Feb. 26, 1987, and in PCT WO 89/05822 published Jun. 29, 1989, i.e., those wherein at least the glutamic acid residue is absent at position 3 from the N-terminus of the mature molecule or those having a deletion of up to five amino acids at the N-terminus. The most preferred variant has the first three amino acids from the N-terminus deleted (variously designated as brain IGF, tIGF-I, des(1-3)-IGF-I, or des-IGF-I).

As used herein, "buffer" refers to a buffered solution that resists changes in pH by the action of its acid-base conjugate components. The buffer for the hydrophobic interaction chromatography aspect of this invention has a pH in a range of about 3–8, preferably about 3–4. Examples of buffers that will control the pH within this range include phosphate, acetate, citrate, ammonium, TRIS, or HEPES buffers, or more than one. The preferred such buffers are citrate and ammonium buffers, most preferably ammonium sulfate or ammonium citrate buffers.

The buffer for the RP-HPLC aspect of this invention has a pH in the range of about 6 to 8. Buffers that will control the pH within this range include, for example, citrate, succinate, phosphate, MES, ADA, BIS-TRIS Propane, PIPES, ACES, imidazole, diethylmalonic acid, MOPS, TES, TRIS buffer such as TRIS-HCl, HEPES, HEPPS, TRICINE, glycine amide, BICINE, glycylglycine, and borate buffers. The preferred buffer is a phosphate buffer. If a buffer other than phosphate buffer is employed, a salt, preferably NaCl or KCl, is added to the buffer in a concentration ranging from about 10 mM up to the solubility limit of the salt.

As used herein, the phrase "phosphate salt" refers to a salt having a cation, preferably from the alkaline earth or alkali metal elements or an ammonium cation, and having a phosphate anion. Examples of such salts include sodium phosphate, calcium phosphate, ammonium phosphate, magnesium phosphate, and potassium phosphate. The most preferred salts herein are sodium and potassium phosphate.

As used herein, "alcohols" and "alcoholic solvents" are meant in the sense of the commonly used terminology for alcohol, preferably alcohols with 1 to 10 carbon atoms, more preferably methanol, ethanol, iso-propanol, n-propanol, or t-butanol, as well as glycerol, propylene glycol, ethylene glycol, polypropylene glycol, and polyethylene glycol, and most preferably ethanol or iso-propanol. Such alcohols are solvents that, when added to aqueous solution, increase the hydrophobicity of the solution by decreasing solution polarity.

"Polar aprotic solvents" are such molecules as dimethyl sulfoxide (DMSO), dimethyl formamide (DMF), N-methylpyrrolidone (NMP), tetrahydrofuran (THF), dioxane, acetonitrile (ACN), etc., that can be used in place of or in addition to the alcohol. The most preferred solvent herein is ACN.

B. Modes for Carrying Out the Invention

The process herein involves purifying IGF-I from its related variants, usually after the IGF-I has already been purified from most other impurities. Hence, this step is typically the final one before desalting or diafiltration prior to therapeutic formulation. While the IGF-I in the mixture of variants may be produced from any source, preferably it is made recombinantly. The related variants include not only variants residual from a fermentation, but also variants produced if the IGF-I is degraded on storage.

If the IGF-I is prepared recombinantly, suitable host cells for expressing the DNA encoding the IGF-I are prokaryote, yeast, or higher eukaryotic cells. Suitable prokaryotes for this purpose include bacteria such as archaebacteria and eubacteria. Preferred bacteria are eubacteria, such as Gram-negative or Gram-positive organisms, for example, Enterobacteriaceae such as Escherichia, e.g., *E. coli*, Enterobacter, Erwinia, Klebsiella, Proteus, Salmonella, e.g., *Salmonella typhimurium*, Serratia, e.g., *Serratia marcescans*, and Shigella; Bacilli such as *B. subtilis* and *B. licheniformis* (e.g., *B. licheniformis* 41P disclosed in DD 266,710 published Apr. 12, 1989); Pseudomonas such as *P. aeruginosa;* Streptomyces; Azotobacter; Rhizobia; Vitreoscilla; and Paracoccus. Suitable *E. coli* hosts include *E. coli* W3110 (ATCC 27,325), *E. coli* 94 (ATCC 31,446), *E. coli* B, and *E. coli* X1776 (ATCC 31,537). These examples are illustrative rather than limiting.

Mutant cells of any of the above-mentioned bacteria may also be employed. It is, of course, necessary to select the appropriate bacteria taking into consideration replicability of the replicon in the cells of a bacterium. For example, *E. coli*, Serratia, or Salmonella species can be suitably used as the host when well known plasmids such as pBR322, pBR325, pACYA177, or pKN410 are used to supply the replicon.

*E. coli* strain W3110 is a preferred host or parent host because it is a common host strain for recombinant DNA product fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonAΔ; *E. coli* W3110 strain 9E4, which has the complete genotype tonAΔ ptr3; *E. coli* W3110 strain 27C7 (ATCC 55,244), which has the complete genotype tonA ptr3 phoAΔE15 Δ(argF-lac)169 ΔdegP ΔompT kan'; *E. coli* W3110 strain 37D6, which has the complete genotype tonA ptr3 phoAΔE15 Δ(argF-lac)169 ΔdegP ΔompT Δrbs7 ilvG kan'; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued Aug. 7, 1990.

In addition to prokaryotes, eukaryotic microbes such as filamentous fungi or yeast are suitable expression hosts for IGF-I-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe* [Beach and Nurse, *Nature*, 290: 140 (1981); EP 139,383 published May 2, 1985]; Kluyveromyces hosts [U.S. Pat. No. 4,943,529; Fleer et al., *Bio/Technology*, 9: 968-975 (1991)] such as, e.g., *K. lactis* [MW98-8C, CBS683, CBS4574; Louvencourt et al., *J. Bacteriol.*, 737 (1983)], *K. fragilis* (ATCC 12,424), *K. bulgaricus* (ATCC 16,045), *K. wickeramii* (ATCC 24,178), *K. waltii* (ATCC 56,500), *K. drosophilarum* [ATCC 36,906; Van den Berg et al., *Bio/Technology*, 8: 135 (1990)], *K. thermotolerans*, and *K. marxianus;* yarrowia [EP 402,226]; *Pichia pastoris* [EP 183,070; Sreekrishna et al., *J. Basic Microbiol.*, 28: 265-278 (1988)]; Candida; *Trichoderma reesia* [EP 244,234]; *Neurospora crassa* [Case et al., *Proc. Natl. Acad. Sci. USA*, 76: 5259-5263 (1979)]; Schwanniomyces such as *Schwanniomyces occidentalis* [EP 394,538 published Oct. 31, 1990]; and filamentous fungi such as, e.g., Neurospora, Penicillium, Tolypocladium [WO 91/00357 published Jan. 10, 1991], and Aspergillus hosts such as *A. nidulans* [Ballance et al., *Biochem. Biophys. Res. Commun.*, 112: 284-289 (1983); Tilburn et al., *Gene*, 26: 205-221 (1983); Yelton et al., *Proc. Natl. Acad. Sci. USA*, 81: 1470-1474 (1984)] and *A. niger* [Kelly and Hynes, *EMBO J.*, 4: 475-479 (1985)].

Suitable host cells appropriate for the expression of the DNA encoding the IGF-I may also be derived from multicellular organisms. Such host cells are capable of complex processing and glycosylation activities. In principle, any higher eukaryotic cell culture is suitable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology*, 6: 47-55 (1988); Miller et al., in *Genetic Engineering*, Setlow, J. K. et al., eds., Vol. 8 (Plenum Publishing, 1986), pp. 277-279; and Maeda et al., *Nature*, 315: 592-594 (1985). A variety of viral strains for transfection are publicly available, e.g., the L-1 variant of *Autographa californica* NPV and the Bm-5 strain of *Bombyx mori* NPV, and such viruses may be used herein, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens*, which have been previously manipulated to contain the DNA encoding the IGF-I. During incubation of the plant cell culture with *A. tumefaciens*, the DNA encoding the IGF-I is transferred to the plant cell host such that it is transfected, and will, under appropriate conditions, express the DNA encoding the IGF-I. In addition, regulatory and signal sequences compatible with plant cells are available, such as the nopaline synthase promoter and polyadenylation signal sequences. Depicker et al., *J. Mol. Appl. Gen.*, 1: 561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

Examples of useful mammalian host cell lines are monkey kidney CV1 line transformed by SV40 (COS-7, ATCC CRL 1651); human embryonic kidney line [293 or 293 cells subcloned for growth in suspension culture, Graham et al., *J. Gen Virol.*, 36: 59 (1977)]; baby hamster kidney cells (BHK, ATCC CCL 10); Chinese hamster ovary cells/-DHFR [CHO, Urlaub and Chasin, *Proc. Natl. Acad. Sci. USA*, 77: 4216 (1980)]; mouse sertoli cells [TM4, Mather, *Biol. Reprod.*, 23: 243-251 (1980)]; monkey kidney cells (CV1, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells [Mather et al., *Annals N.Y. Acad. Sci.*, 383: 44–68 (1982)]; MRC 5 cells; FS4 cells; and a human hepatoma line (Hep G2).

Host cells are transfected and preferably transformed with the above-described expression or cloning vectors and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., *Molecular Cloning: A Laboratory Manual* [New York: Cold Spring Harbor Laboratory Press, 1989], or electroporation is generally used for prokaryotes or other cells that contain substantial cell-wall barriers. Infection with *Agrobacterium tumefaciens* is used for transformation of certain plant cells, as described by Shaw et al., *Gene*, 23: 315 (1983) and WO 89/05859 published Jun. 29, 1989. In addition, plants may be transformed using ultrasound treatment as described in WO 91/00358 published Jan. 10, 1991.

For mammalian cells without such cell walls, the calcium phosphate precipitation method of Graham and van der Eb, *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., *J. Bact.*, 130: 946 (1977) and Hsiao et al., *Proc. Natl. Acad. Sci. (USA)*, 76: 3829 (1979). However, other methods for introducing DNA into cells, such as by nuclear microinjection, electroporation, bacterial protoplast fusion with intact cells, or polycations, e.g., polybrene, polyornithine, etc., may also be used. For various techniques for transforming mammalian cells, see Keown et al., *Methods in Enzymology* (1990) Vol. 185, pp. 527–537, and Mansour et al., *Nature*, 336: 348–352 (1988).

If prokaryotic cells are used to produce IGF-I, they are cultured in suitable media in which the promoter can be constitutively or artificially induced as described generally, e.g., in Sambrook et al., *Molecular Cloning: A Laboratory Manual* (Cold Spring Harbor Laboratory Press, New York 1989). Examples of suitable media are given below in the example section.

Any necessary supplements besides carbon, nitrogen, and inorganic phosphate sources may also be included at appropriate concentrations introduced alone or as a mixture with another supplement or medium such as a complex nitrogen source. The pH of the medium may be any pH from about 5–9, depending mainly on the host organism.

If mammalian host cells are used to produce IGF-I, they may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, *Meth. Enz.*, 58: 44 (1979); Barnes and Sato, *Anal. Biochem.*, 102: 255 (1980); U.S. Pat. Nos. 4,767,704; 4,657,866; 4,927,762; 5,122,469; or 4,560,655; WO 90/03430; WO 87/00195; or U.S. Pat. No. Re. 30,985, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin TM drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

In general, principles, protocols, and practical techniques for maximizing the productivity of in vitro mammalian cell cultures can be found in *Mammalian Cell Biotechnology: A Practical Approach*, M. Butler, ed. (IRL Press at Oxford University Press, Oxford, 1991).

The above process can be employed whether the IGF-I is produced intracellularly, produced in the periplasmic space, or directly secreted into the medium. In one example of the embodiment where the IGF-I is directly secreted into the medium, at the end of the fermentation the cells are heat-killed and inactivated and the medium is separated from the cellular debris by centrifugation. The clarified fermentation broth is then used for purification on silica.

For the silica chromatography, typically the broth is passed through underivatized silica particles such that the polypeptide adheres to the silica particles; the silica particles are washed to remove contaminants; and the polypeptide is eluted from the silica particles with a buffer comprising an alcoholic or polar aprotic solvent and an alkaline earth, an alkali metal, or an inorganic ammonium salt. Preferably, the buffer is at pH of about 5–8 comprising about 5–40% (v/v) of an alcoholic or polar aprotic solvent and about 0.2 to 3M of an alkaline earth, an alkali metal, or an inorganic ammonium salt.

In one example of the embodiment where the IGF-I is produced in the periplasmic space, the culture medium or lysate is centrifuged to remove particulate cell debris. The membrane and soluble protein fractions may then be separated if necessary. The IGF-I may then be purified from the soluble protein fraction and from the membrane fraction of the culture lysate, depending on whether the IGF-I is membrane bound, is soluble, or is present in an aggregated form. The IGF-I thereafter is solubilized and then subsequently refolded using an appropriate buffer. The details for this method of isolation from the periplasm to produce refolded protein are described below.

Insoluble, non-native IGF-I is isolated from the prokaryotic host cells in a suitable isolation buffer by any appropriate technique, e.g., one involving exposing the cells to a buffer of suitable ionic strength to solubilize most host proteins, but in which aggregated IGF-I is substantially insoluble, and disrupting the cells so as to release the inclusion bodies and make them available for recovery by, for example, centrifugation. This technique is well known, and is described, for example, in U.S. Pat. No. 4,511,503.

Briefly, the cells are suspended in the buffer (typically at pH 5 to 9, preferably about 6 to 8, using an ionic strength of about 0.01 to 2M, preferably 0.1 to 0.2M). Any suitable salt, including sodium chloride, is useful to maintain a sufficient ionic strength value. The cells, while suspended in this buffer, are then disrupted by lysis using techniques commonly employed such as, for example, mechanical methods, e.g., a Manton-Gaulin press, a French press, or a sonic oscillator, or by chemical or enzymatic methods.

Examples of chemical or enzymatic methods of cell disruption include spheroplasting, which entails the use of lysozyme to lyse the bacterial wall [Neu et al., Biochem. Biophys. Res. Comm., 17: 215 (1964)], and osmotic shock, which involves treatment of viable cells with a solution of high tonicity and with a cold-water wash of low tonicity to release the polypeptides [Neu et al., J. Biol. Chem., 240: 3685–3692 (1965)]. A third method, described in U.S. Pat. No. 4,680,262, involves contacting the transformed bacterial cells with an effective amount of a lower alkanol having 2 to 4 carbon atoms for a time and at a temperature sufficient to kill and lyse the cells.

After the cells are disrupted, the suspension is typically centrifuged to pellet the inclusion bodies. In one embodiment, this step is carried out at about 500 to 15,000×g, preferably about 12,000×g, in a standard centrifuge for a sufficient time that depends on volume and centrifuge design, usually about 10 minutes to 0.5 hours. The resulting pellet contains substantially all of the insoluble polypeptide fraction, but if the cell disruption process is not complete, it may also contain intact cells or broken cell fragments. Completeness of cell disruption can be assayed by resuspending the pellet in a small amount of the same buffer solution and examining the suspension with a phase-contrast microscope. The presence of broken cell fragments or whole cells indicates that additional disruption is necessary to remove the fragments or cells and the associated non-refractile polypeptides. After such further disruption, if required, the suspension is again centrifuged and the pellet recovered, resuspended, and analyzed. The process is repeated until visual examination reveals the absence of broken cell fragments in the pelleted material or until further treatment fails to reduce the size of the resulting pellet.

In an alternative embodiment, the IGF-I is isolated from the periplasmic space by solubilization in a suitable buffer. This procedure can be in-situ solubilization involving direct addition of reagents to the fermentation vessel after the IGF-I has been produced recombinantly, thereby avoiding extra steps of harvesting, homogenization, and centrifugation to obtain the IGF-I. The remaining particulates can be removed by centrifugation or filtration, or combinations thereof. Alternatively, and more preferably, one may use a multiple-phase isolation/extraction system for purifying IGF-I from the remaining particulates.

In the aqueous multiple-phase isolation system, one or more denaturants (chaotropic agent), such as urea, guanidine hydrochloride, and/or a base, and a reducing agent, such as dithiothreitol or cysteine, are added to the IGF-I-containing medium at basic pH and then phase-forming species are added to the broth. Once this second group of reagents is added to the broth, multiple phases are formed whereby one phase is enriched in the IGF-I and depleted in biomass solids and nucleic acids. Preferably, the system has two to four phases, and more preferably two phases, one being enriched in IGF-I and the other being enriched in biomass solids and nucleic acids. Preferably, the IGF-I partitions to the upper phase so that the upper phase is enriched in the IGF-I and depleted in the biomass solids and nucleic acids.

Thus, after fermentation is complete, the cell culture is contacted with one or more chaotropic agents, an optional reducing agent, and phase-forming reagents so that multiple phases are formed, one phase of which is enriched in IGF-I. It is preferred to add the chaotrope and reducing agent first to extract the IGF-I from the cell and maintain its solubility in the broth before the phase-forming reagents are added. Also, while the IGF-I can be extracted from (and enriched in) any phase, preferably it is recovered from the uppermost phase.

Most preferably, the chaotropic agent and optional reducing agent are added directly to the fermentation broth in the fermentation vessel before isolation of the IGF-I so that the reagents permeate the cells and the IGF-I is solubilized and diffuses to the surrounding medium.

Examples of suitable reducing agents include dithiothreitol (DTT), $\beta$-mercaptoethanol (BME), cysteine, thioglycolate, and sodium borohydride. The amount of reducing agent to be present in the buffer will depend mainly on the type of reducing agent and chaotropic agent, the type and pH of the buffer employed, and the type and concentration of the IGF-I in the buffer. An effective amount of reducing agent is that which is sufficient to eliminate intermolecular disulfide-mediated aggregation. For example, with 0.5–6 mg/mL IGF-I in a buffered solution at pH 7.5–10.5 containing 1–4M urea, the DTT concentration is at about 1–20 mM, and the concentration of cysteine is at about 10–50 mM. The preferred reducing agents are DTT at about 2–10 mM and cysteine at about 30–50 mM.

Suitable chaotropic agents include, e.g., urea and salts of guanidine or thiocyanate, more preferably urea, guanidine hydrochloride, or sodium thiocyanate. The amount of chaotropic agent necessary to be present in the buffer depends, for example, on the type of chaotropic agent present. The amount of chaotropic agent to be added to the fermentation broth will be sufficiently high to extract the IGF-I from the cell and maintain its solubility in the broth. If the IGF-I is to be extracted from the top phase, the amount of chaotropic agent must be sufficiently low so that after addition of the phase-forming species, the density is not increased to a point where the solids rise to the top instead of settling to the bottom. Generally the concentration of chaotropic agent is about 0.1 to 9M, preferably about 0.5–9M, more preferably about 0.5 to 6M, and most preferably about 0.5–3M. Also, preferably the chaotropic agent is added to the culture medium before the phase-forming reagents are added. The preferred chaotropic agent herein is urea at about 1.5–2.5M, more preferably at about 2M, or guanidine hydrochloride at about 0.5–3M. Most preferably, the chaotropic agent is urea.

The concentration of IGF-I in the aqueous solution to which the chaotrope and reducing agent are added must be such that the IGF-I will be recovered in the maximum yield. The exact amount to employ will depend, e.g., on the concentrations and types of other ingredients in the aqueous solution, particularly the reducing agent, chaotropic agent, phase-forming species, and pH. The preferred concentration of IGF-I (resulting in the maximum yield of denatured or non-native IGF-I) is in the range of 0.5–6 mg per mL, more preferably 1.5–5 mg/mL.

The types of phase-forming species to employ herein depend on many factors, including the type of ingredients in the fermentation broth being treated. The species must be selected so that the IGF-I does not precipitate and one phase is more hydrophobic than the other phase so that the IGF-I will be located in the more hydrophobic phase and the biomass solids and nucleic acids will settle to the less hydrophobic phase.

The phase-forming species may be a combination of agents, including polymer combinations (polymer-polymer), polymer-salt combinations, solvent-salt combinations, and polymer-solvent combinations. Suitable polymers are both highly hydrophilic polymers and less hydrophilic polymers, i.e., any phase-forming polymers that are known in the art. Examples include polyethylene glycol (PEG) or derivatives thereof, including various molecular weights of PEG such as PEG 4000, PEG 6000, and PEG 8000, derivatives of PEG described, for example, in Grunfeld et al., *Appl. Biochem. Biotechnol.*, 33: 117–138 (1992), polyvinylpyrrolidone (PVP), in a preferable molecular weight range of about 36,000 to 360,000, starches such as dextran (e.g., dextran 70 and 500), dextrins, and maltodextrins (preferable molecular weight between about 600 and 5,000), sucrose, and Ficoll-400 TM polymer (a copolymer of sucrose and epichlorohydrin). The preferred polymer herein is polyethylene glycol, polypropylene glycol, polyvinylpyrrolidone, or a polysaccharide such as a dextran. The most preferred polymer herein is PEG of different molecular weights or a PEG-polypropylene glycol combination or copolymer.

Examples of suitable organic solvents include ethylene glycol, glycerol, dimethyl sulfoxide, polyvinylalcohol, dimethylformamide, dioxane, and alcohols such as methanol, ethanol, and 2-propanol. Solvents are chosen such that, when added to aqueous solution, they increase the hydrophobicity of the solution.

The salts can be inorganic or organic and preferably do not act to precipitate the IGF-I. Salts containing transition elements are not preferred as they tend to precipitate the IGF-I. Anions are selected that have the potential for forming aqueous multiple-phase systems. Examples include ammonium sulfate, sodium dibasic phosphate, sodium sulfate, ammonium phosphate, potassium citrate, magnesium phosphate, sodium phosphate, calcium phosphate, potassium phosphate, potassium sulfate, magnesium sulfate, calcium sulfate, sodium citrate, manganese sulfate, manganese phosphate, etc. Types of salts that are useful in forming bi-phasic aqueous systems are evaluated more fully in Zaslavskii et al., *J. Chrom.*, 439: 267–281 (1988). Preferred salts herein are sulfates, phosphates, or citrates and are alkali or alkaline earth metals. More preferred are sulfates and citrates, and most preferred are sulfates since there are fewer pH limitations with sulfates. The most preferred salts herein are sodium sulfate and sodium citrate.

The amounts of phase-forming species to add to the IGF-I to obtain a satisfactory multiple-phase system are those known in the art. The amount of phase-forming species added to the IGF-I will depend on such factors as, for example, the amount of chaotropic agent and reducing agent, if any, already present in the fermentation broth, the nature of the cell culture media, the type of cells used in the fermentation, whether the IGF-I will be recovered from the lower or upper phase, and the type(s) of phase-forming species being added. The general concentration of polymer employed is about 5% (w/w) up to the limit of solubility for the polymer and the concentration of salt employed is about 3% (w/w) up to the limit of solubility for the salt, depending on the size of the phase-volume ratio needed. The phase-volume ratio must be sufficient to accomodate the biomass solids. The types and amounts of phase-forming species that are effective can be determined by phase diagrams and by evaluating the final result, i.e., the degree of purity and the yield of the IGF-I. If the phase-forming species are a polymer-salt combination, preferably the concentration of salt added is about 4–15% (w/w) and the concentration of polymer is 5–18% (w/w) so that the IGF-I will be in an opposite phase from that in which the biomass solids and nucleic acids are present.

If the system desired is one where the IGF-I is distributed in the top phase and the biomass solids and nucleic acids are in the bottom phase, then there is a window of concentrations of phase-forming species. The higher the amounts of chaotropic agent added to maintain solubilization, the higher the amount of phase-forming species required. However, a high concentration of all these reagents will increase the density of the solution. A high density will cause the biomass solids to settle less readily. An overly high density will cause biomass solids to float on the surface. Hence, the concentrations of chaotropic agent and phase-forming species must be sufficiently high to maintain a fully solubilized IGF-I, but low enough to allow the biomass solids and nucleic acids to sediment to the opposite (lower) phase.

If the IGF-I is to be recovered in the upper phase, typically the salt concentration will be about 4–7% (w/w) and the polymer concentration will be about 12–18% (w/w), depending, e.g., on the type of salt and polymer. If an organic solvent is added as a phase-forming species, such as ethanol, it is preferably added in an amount of about 10 to 30% (volume/volume) of the solution, depending, e.g., on the type of alcohol and if any other phase-forming species is present, preferably at a concentration of about 20% (v/v).

The exact conditions for contacting the cell culture with the various reagents will depend, e.g., on the pH of the buffer, the types of phase-forming reagents, and the types and concentrations of chaotropic and reducing agents and the concentration of IGF-I. The reaction temperature is generally about 20°–40° C., more preferably room temperature. The contacting step will generally be carried out for at least about 30 minutes, preferably about 30 minutes to 12 hours depending on whether side-reactions will occur, more preferably about 30 minutes to 8 hours, and most preferably about 30 minutes to 1.5 hours.

If the IGF-I is being unfolded, the degree of unfolding is suitably determined by chromatography of the non-native IGF-I, including RP-HPLC. Increasing peak area for the non-native material indicates how much non-native IGF-I is present.

Once the multiple-phase system is established, one phase will be enriched in the IGF-I and depleted in the disrupted particles and cells comprising the biomass solids and nucleic acids. In a two-phase system, preferably the top phase is enriched in the IGF-I, whereas the bottom phase is enriched in the disrupted particles and cells. The IGF-I can be easily recovered by separation of the phases. This recovery step may be accomplished by decanting the upper phase, by draining the lower phase, or by centrifugation. The IGF-I can then be isolated from the phase in which it is contained by changing the pH of the phase so as to precipitate the IGF-I or by adding a suitable solvent, whereupon the precipitated IGF-I is suitably recovered by centrifugation or filtration or as a slurry. Alternatively, the IGF-I can be recovered from the polymer-containing phase by re-extraction by addition of a suitable polymer, salt, or solvent. IGF-I is preferably recovered from the isolated polymer phase by lowering the pH so that the IGF-I will precipitate, resulting in a yield of IGF-I of as much as or more than about 96%.

Once obtained from the liquid phase of the multiple-phase system, or at a later stage of purification, the IGF-I is suitably refolded into an active conformation as described below.

If the IGF-I is not already in soluble form before it is to be refolded, it may be solubilized by incubation in alkaline buffer containing chaotropic agent and reducing agent in amounts necessary to substantially solubilize the IGF-I. This incubation takes place under conditions of IGF-I concentration, incubation time, and incubation temperature that will allow solubilization of the IGF-I to occur in the alkaline buffer.

Measurement of the degree of solubilization of the IGF-I in the buffer is suitably carried out by turbidity determination, by analyzing IGF-I fractionation between the supernatant and pellet after centrifugation on reduced SDS gels, by protein assay (e.g., the Bio-Rad protein assay kit), or by HPLC.

The pH range of the alkaline buffer for solubilization typically is at least about 7.5, with the preferred range being about 8–11. Examples of suitable buffers that will provide a pH within this latter range include glycine, CAPSO (3-[Cyclohexylamino]-2-hydroxy-1-propanesulfonic acid), AMP (2-Amino-2-methyl-1-propanol), CAPS (3-[Cyclohexylamino]-1-propanesulfonic acid), CHES (2-[N-Cyclohexylamino]ethanesulfonic acid), and TRIS HCl (Tris[hydroxymethyl]aminomethane hydrochloride. The preferred buffer herein is glycine or CAPSO, preferably at a concentration of about 20 mM, at a pH of about 8.5 to 11, preferably about 10–11.

The concentration of IGF-I in the buffered solution for solubilization must be such that the IGF-I will be substantially solubilized and partially or fully reduced and denatured. Alternatively, the IGF-I may be initially insoluble. The exact amount to employ will depend, e.g., on the concentrations and types of other ingredients in the buffered solution, particularly the type and amount of reducing agent, the type and amount of chaotropic agent, and the pH of the buffer. For example, the concentration of IGF-I may be increased at least threefold if the concentration of reducing agent, e.g., DTT, is concurrently increased, to maintain a ratio of DTT:IGF-I of from about 3:1 to 10:1. It is desirable to produce a more concentrated solubilized protein solution prior to dilution refolding. Thus, the preferred concentration of IGF-I is at least about 30 mg/mL, with a more preferred range of 30–50 mg per mL. For example, IGF-I may be solubilized to a concentration of about 30–50 mg/mL in 2M urea, 10 mM DTT and diluted to, for example, about 1 mg/mL for folding.

After the IGF-I is solubilized, it is placed or diluted into a refolding buffer containing 5–40% (v/v) alcoholic or aprotic solvent, a chaotropic agent, and an alkali metal, alkaline earth, or ammonium salt. The buffer can be any buffer for the first buffered solution, with CAPSO, glycine, and CAPS being preferred at pH 8.5–11, particularly at a concentration of about 20 mM, and most preferably CAPSO and glycine. The IGF-I may be diluted with the refolding buffer, preferably at least five fold, more preferably at least about ten fold. Alternatively, the IGF-I may be dialyzed against the refolding buffer. The refolding is typically carried out at about 0°–45° C., preferably about 20°–40° C., more preferably about 23°–37° C., even more preferably about 25°–37° C., and most preferably about 25° C. for at least about one hour. The preferred temperature is not apparently affected by salt, solvent, and chaotropic agent levels, but may be affected by the presence of sucrose and glycerol, in which case it should be kept above about 20° C. The solution optionally also contains a reducing agent and an osmolyte.

The reducing agent is suitably selected from those described above for the solubilizing step in the concentration range given. Its concentration will depend especially on the concentrations of alkaline earth, alkali metal, or ammonium salt, IGF-I, and solvent. Preferably, the concentration of reducing agent is about 0.5 to 8 mM, more preferably about 0.5–5 mM, even more preferably about 0.5–2 mM. The preferred reducing agents are DTT and cysteine.

The optional osmolyte is preferably sucrose (in a concentration of about 0.25–1M) or glycerol (in a concentration of about 1–4M). More preferably, the sucrose concentration is at about 1M and the glycerol concentration is at about 4M.

The initial concentration of IGF-I in the folding buffer is such that the ratio of correctly folded to misfolded conformer recovered will be maximized, as determined by HPLC, RIA, or bioassay. The preferred concentration of IGF-I (resulting in the maximum yield of correctly folded conformer) is in the range of about 0.1 to 15 mg/mL, more preferably about 0.1 to 6 mg/mL, and most preferably about 0.2 to 5 mg/mL.

In addition, a source of oxygen such as air or oxygen gas is entrained in or otherwise introduced into the buffer so as to effect oxidation together with the copper or manganese salt. The oxygen can be present in the buffer at any point in time, including before the IGF-I or any other reagents are added to the buffer.

The amount of oxygen source introduced will depend, e.g., on the type of vessel utilized, the concentration of IGF-I, the type of oxygen source, the type and amount of copper or manganese salt, the type and amount of reducing agent present, if any, and the type and amount of chaotropic agent present as well as the pH of the buffer. Generally, the oxygen source will be introduced by passive means (e.g., as air in head space in a ratio of air space to fluid volume of 2:1) using an agitator. Alternatively, the oxygen source may be introduced by bubbling through a sparger. The rate of introduction of the oxygen must be sufficient to allow folding to reach completion in preferably about 1 to 12 hours, more preferably about 1 to 6 hours, and most preferably about 1 to 3 hours. The addition of molar oxygen is proportional to the reductant concentration and IGF-I concentration, but inversely proportional to the copper or magnesium salt concentration. The rate of oxidation is limited by the level of catalyst, not by the oxygen addition rate. A higher sparging rate is required for larger volume folding.

The degree of refolding that occurs upon this second incubation is suitably determined by the RIA titer of the IGF-I or by HPLC analysis using e.g., a Vydac or Baker C-18 column, with increasing RIA titer or correctly folded IGF-I peak size directly correlating with increasing amounts of correctly folded, biologically active IGF-I conformer present in the buffer. The incubation is carried out to maximize the yield of correctly folded IGF-I conformer and the ratio of correctly folded IGF-I conformer to misfolded IGF-I conformer recovered, as determined by RIA or HPLC, and to minimize the yield of multimeric, associated IGF-I as determined by mass balance.

After the IGF-I is refolded, the following procedures, individually or in combination, are exemplary of suitable purification procedures for obtaining greater purity: fractionation on immunoaffinity or ion-exchange columns; ethanol precipitation; reversed-phase HPLC; hydrophobic interaction chromatography; chromatography on silica; chromatography on an ion-exchange resin such as S-SEPHAROSE TM agarose and DEAE; chromatofocusing; SDS-PAGE; ammonium sulfate precipitation; and gel filtration using, for example, Sephadex G-75.

In a preferred embodiment, the clarified, folded pool is pH adjusted to about 3–8, preferably 3–5, more preferably 3.5, and loaded directly onto a low-pressure reversed-phase column. The loading buffer preferably comprises about 5–40% (v/v), preferably 10–30%, of an alcoholic or polar aprotic solvent and about 0.2 to 3M, preferably about 0.5 to 2M, of an alkaline earth or alkali metal salt. Preferably, the solvent is methanol, ethanol, isopropanol, n-propanol, t-butanol, dimethylsulfoxide, dimethylformamide, N-methylpyrrolidone, tetrahydrofuran, dioxane, or ACN, and the alkaline earth or alkali metal salt is a sodium or potassium salt. More preferably, the solvent is ethanol and the sodium or potassium salt is a chloride or sulfate salt. The loading buffer may also contain a chaotropic agent such as urea or guanidine hydrochloride, preferably urea, at a concentration of about 1 to 5M.

The column is then washed with a buffer at pH preferably about 3 to remove impurities, and the IGF-I is eluted with a gradient or increasing percentage of about 0 to 40% (v/v) of the solvent containing about 0.02 to 0.1M of the salt in a buffer at preferably about pH 3. The pH 3 buffer is preferably acetic acid. Preferably, the elution is achieved using a buffer of 50 mM acetic acid, 50 mM sodium chloride, and a linear gradient from 28 to 32% (v/v) ethanol.

This pool from either the silica column or the low-pressure reversed-phase column is then loaded on a cation-exchange column such as a S-SEPHAROSE TM agarose column. After washing, which can be done with Tris buffer, the column is eluted with a buffered salt at a pH of about 5–7, such as a citrate buffer at pH 6.

While the resulting pool can then be subjected directly to the reversed-phase liquid chromatography step of this invention, preferably another step is performed to purify the IGF-I further before the liquid chromatography step. In this intermediate step, the pool is adjusted with a salt such as ammonium sulfate and then loaded onto a hydrophobic interaction chromatography column in a buffer at a pH of about 3–8. Preferably, this buffer contains about 0.2 to 1M of a salt. The column is then washed with a buffer at a pH of about 3–8, with the buffer preferably containing about 0.1 to 1M of a salt. The IGF-I is then eluted with a step gradient of decreasing salt or pH using a buffer at a pH of about 3–8, with this buffer optionally containing a salt in the range of about 0 to 0.4M. Preferably, the hydrophobic interaction column is a phenyl column, more preferably a phenyl Toyopearl column.

Starting with a partially purified process pool, such as those mentioned above, the mixture of IGF-I and its variants is loaded onto a reversed-phase liquid chromatography column. Preferably, this column is a RP-HPLC column, but it need not be. The column may be preparative or analytical. The loading solvent may be any solvent but is preferably an alcoholic or polar aprotic solvent. More preferably, the solvent is at a concentration of about 5–20% (v/v), more preferably 10 to 20% (v/v) of the solution, depending, e.g., on the type of solvent. If the concentration is too high, the IGF-I flows through the column.

Preferably, the column is packed with a medium having a particle diameter of about 5–40 $\mu$m, more preferably about 10–15 $\mu$m, and a pore size of about 100–4000 Å, more preferably about 150–300 Å. Also, the medium preferably has a C4, C8, or C18 alkyl group, and most preferably is a C4 silica medium.

The amount of IGF-I loaded onto the column is generally about 0.01 to 40 mg IGF-I/mL bed volume, more preferably about 0.02 to 30 mg IGF-I/mL bed volume, and most preferably about 1 to 10 mg IGF-I/mL bed volume.

In the second step of the process herein, the IGF-I is eluted from the column with a buffer at a pH of about 6–8 containing an alcoholic or polar aprotic solvent in a concentration of about 20–30% (v/v). Preferably, the buffer is a phosphate buffer, although other buffers may be employed as indicated in the Definition Section above, provided that they maintain the pH in the range of about 6–8. If the buffer is other than phosphate buffer, preferably sodium chloride is added in an amount of from about 10 mM up to the solubility limit of the sodium chloride.

If the buffer is a phosphate buffer, preferably the phosphate is at a concentration of about 10 mM to the solubility limit of the salt. More preferably, the concentration of the phosphate salt in the preferred buffer is about 10–200 mM, more preferably about 15–150 mM. Most preferably, the buffer is about 100 mM sodium or potassium phosphate, pH adjusted to about 7. Preferably, this pH adjustment is accomplished using HCl.

The temperature of the elution is generally about 30°–60° C., although higher or lower temperatures may be employed. Preferably, the temperature is maintained at about 45° to 55° C.

While the solvent contained in the buffer can be any alcoholic or polar aprotic solvent as set forth above, in a preferred embodiment, the solvent is ACN. If ACN is employed as the solvent, it is preferably used in a gradient of about 0 to 2% (v/v) per 5–9 column volumes, starting with an ACN concentration of about 20–28% (v/v).

After the IGF-I is eluted from the column, it is suitably formulated into a pharmaceutical composition as follows. The eluate is pH adjusted to a range of about 3–5, preferably 3.5, loaded on a cation-exchange column such as S-Sepharose or S-SEPHAROSE TM agarose or SP-SEPHAROSE TM agarose washed, and eluted with a buffered salt at about pH 5–6, such as citrate. After this step the IGF-I is formulated with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides. This formulation step is achieved by desalting or diafiltering using standard technology.

Generally, the formulations are prepared by contacting the IGF-I uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeprides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counter-ions such as sodium; and/or nonionic surfactants such as polysorbates, poloxamers, or PEG.

The IGF-I is typically formulated in such vehicles at a concentration of about 0.1 mg/mL to 100 mg/mL, preferably 1 to 10 mg/mL, at a pH of about 3 to 8. Full-length IGF-I is generally most stable at a pH of about 6; des(1-3)-IGF-I is generally most stable at a pH about 3.2 to 5. It will be understood that use of certain of the foregoing excipients, carriers, or stabilizers will result in the formation of IGF-I salts.

In addition, the IGF-I, preferably the full-length IGF-I, is suitably formulated in an acceptable carrier vehicle to form a pharmaceutical composition. If this formulation is to be stored, it is preferably formulated in a buffer at a pH of about 6, such as citrate, with a surfactant that increases the solubility of the IGF-I at this pH, such as 0.1% polysorbate 20 or poloxamer 188. The final preparation may be a liquid or lyophilized solid.

IGF-I to be used for therapeutic administration must be sterile. Sterility is readily accomplished by filtration through sterile filtration membranes (e.g., 0.2 micron membranes). Therapeutic IGF-I compositions generally are placed into a container having a sterile access port, for example, an intravenous solution bag or vial having a stopper pierceable by a hypodermic injection needle.

IGF-I ordinarily will be stored in unit or multi-dose containers, for example, sealed ampoules or vials, as an aqueous solution, or as a lyophilized formulation for reconstitution. As an example of a lyophilized formulation, 10-mL vials are filled with 5 mL of sterile-filtered 1% (w/v) aqueous IGF-I solution, and the resulting mixture is lyophilized. The infusion solution is prepared by reconstituting the lyophilized IGF-I using bacteriostatic Water-for-Injection.

The invention will be more fully understood by reference to the following examples, which are intended to illustrate the invention but not to limit its scope. All literature and patent citations are expressly incorporated by reference.

EXAMPLE I

In this example, IGF-I is periplasmically secreted and partially purified.

A. Construction of host cell strain 37D6

The host used to produce recombinant human IGF-I in the fermentation described in this example was a derivative of E. coli W3110, designated 37D6. The complete genotype of 37D6 is tonA ptr3 phoA$\Delta$E15 $\Delta$(argF-lac)169 $\Delta$degP $\Delta$ompT $\Delta$rbs7 ilvG kan$^r$. The derivation of strain 27C7, which is a parent strain for 37D6 having the genotype tonA ptr3 phoA$\Delta$E15 $\Delta$(argF-lac)169 $\Delta$degP $\Delta$ompT kan$^r$, is set forth in WO 93/11240 published Jun. 10, 1993, the disclosure of which is incorporated herein by reference. Strain 27C7 was deposited on Oct. 30, 1991 in the American Type Culture Collection as ATCC No. 55,244.

Strain 37D6 is the same as 27C7 described above except for having a rbs7 deletion (ribose utilization minus) and having a restored ilvG locus. Both markers can be introduced by P1 transduction.

B. Description/Construction of IGF-I Expression Plasmid pBKIGF2B

In the IGF-I-expressing plasmid pBKIGF-2B, the transcriptional and translational sequences required for expression of the IGF-I gene in E. coli are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamB signal sequence or alternatively by the STII signal sequence. The majority of rhIGF-I is found in the cell periplasmic space. Plasmid pBKIGF-2B confers tetracycline resistance upon the transformed host.

Plasmid pBKIGF-2B was constructed in several steps using as intermediate plasmids pLS32Tsc, pLBIGFTsc, pLS33Tsc, and pRanTsc.

Step 1: pLS32Tsc

The secretion plasmid pLS32Tsc contains the IGF-I gene. The transcriptional and translational sequences required for expression of the IGF-I gene in E. coli are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamb signal sequence or alternatively by the STII signal sequence. The majority of rhIGF-I is found in the cell periplasmic space. Plasmid pLS32Tsc confers tetracycline resistance upon the transformed host.

Plasmid pLS32Tsc was constructed in several steps using as intermediate plasmids pLS32, pAPlamB, pLS32lamB, pLS33llamB, and pLS33Tsc as disclosed in detail in WO 93/11240, supra.

Step 2: pLBIGFTsc

Step a: pLamBIGF

For the first part of the ligation, the EcoRI-PstI vector fragment from pBR322 was isolated. For the second part of the ligation, a PstI-NcoI 1244-bp fragment was isolated from pAPLamB. For the third part of the ligation, the HaeII-EcoRI 196-bp fragment containing the IGF-I gene except the initial 5' end was isolated from plasmid p200. p200 is a pBR322-derived plasmid having, in the 5' to 3' order, the chelatin promoter, the MF alpha I prepro signal sequence, DNA encoding mature IGF-I, and the 2-micron terminator. It contains the ColE1 origin of replication for bacteria and the 2-micron origin for yeast. A restriction enzyme plasmid diagram of p200 is provided in FIG. 1. The nucleotide sequence (SEQ. ID NO. 1) of the EcoRI (starting at position 1149) to EcoRI (starting at position 1628) fragment of p200 containing the MF alpha I prepro and IGF-I gene is provided in FIG. 2. The HaeII, PstI, BamHI, and SalI restriction sites that are also in the diagram in FIG. 2 are indicated in the sequence by underlining. A piece of synthetic DNA linking the signal sequence to the IGF-I gene (NcoI to HaeII) was prepared having the following sequence:

5'-CATG GCC GGT CCG GAA ACT CTG TGC
GGC GC                                    (SEQ. ID NO. 2)

3'-CGG CCA GGC CTT TGA GAC ACG C (SEQ. ID NO. 3).

Figure 3:
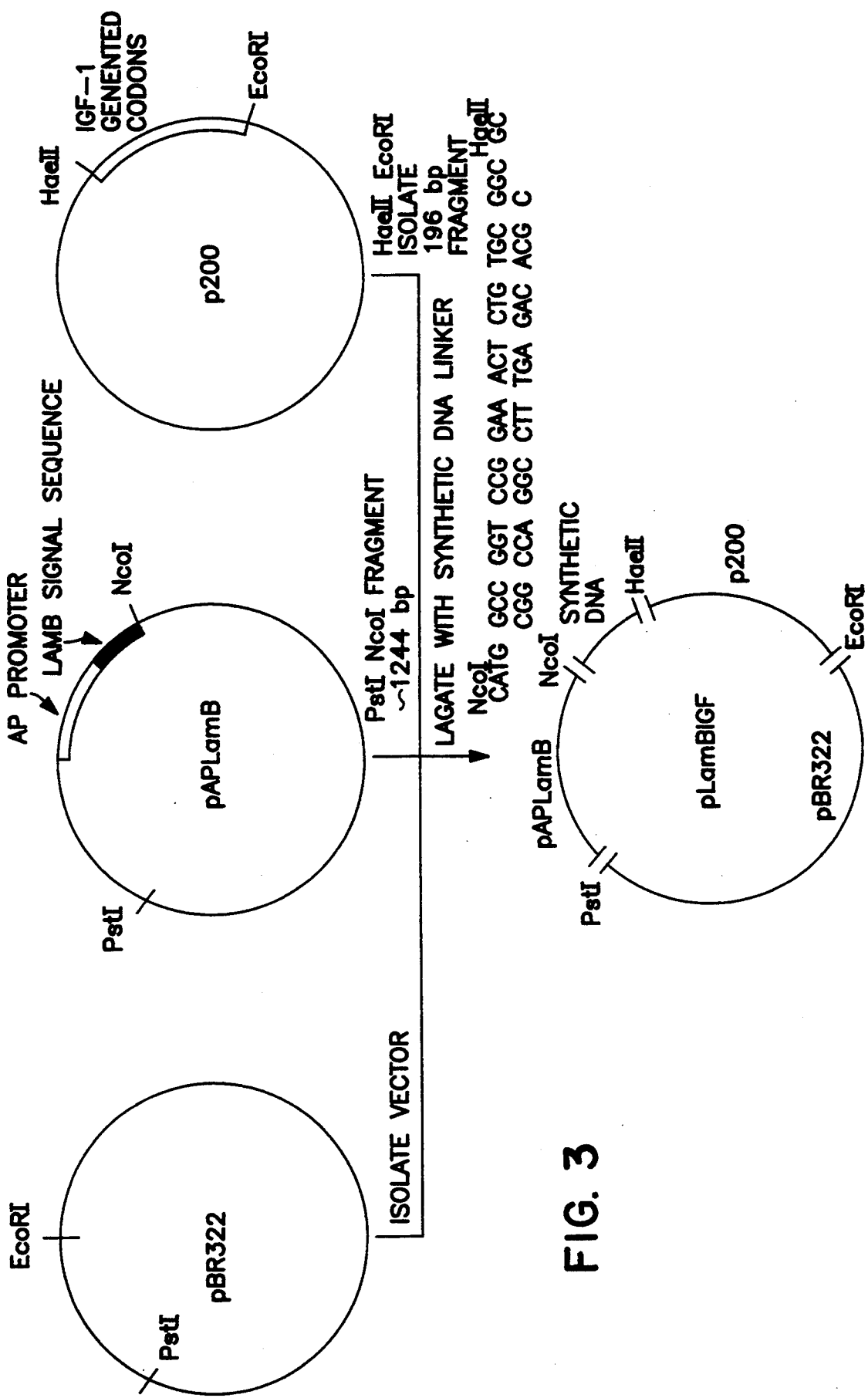
FIG. 3 depicts the construction of pLamBIGF from three plasmid fragments and a piece of synthetic DNA (SEQ. ID NOS. 2 and 3). pLamBIGF is an intermediate plasmid in the production of pLBIGFTsc, used to prepare pBKIGF-2.

The three plasmid fragments and the synthetic DNA were ligated together to form pLamBIGF, as shown in FIG. 3.

Step b: pLBIGFTsc

Figure 4:
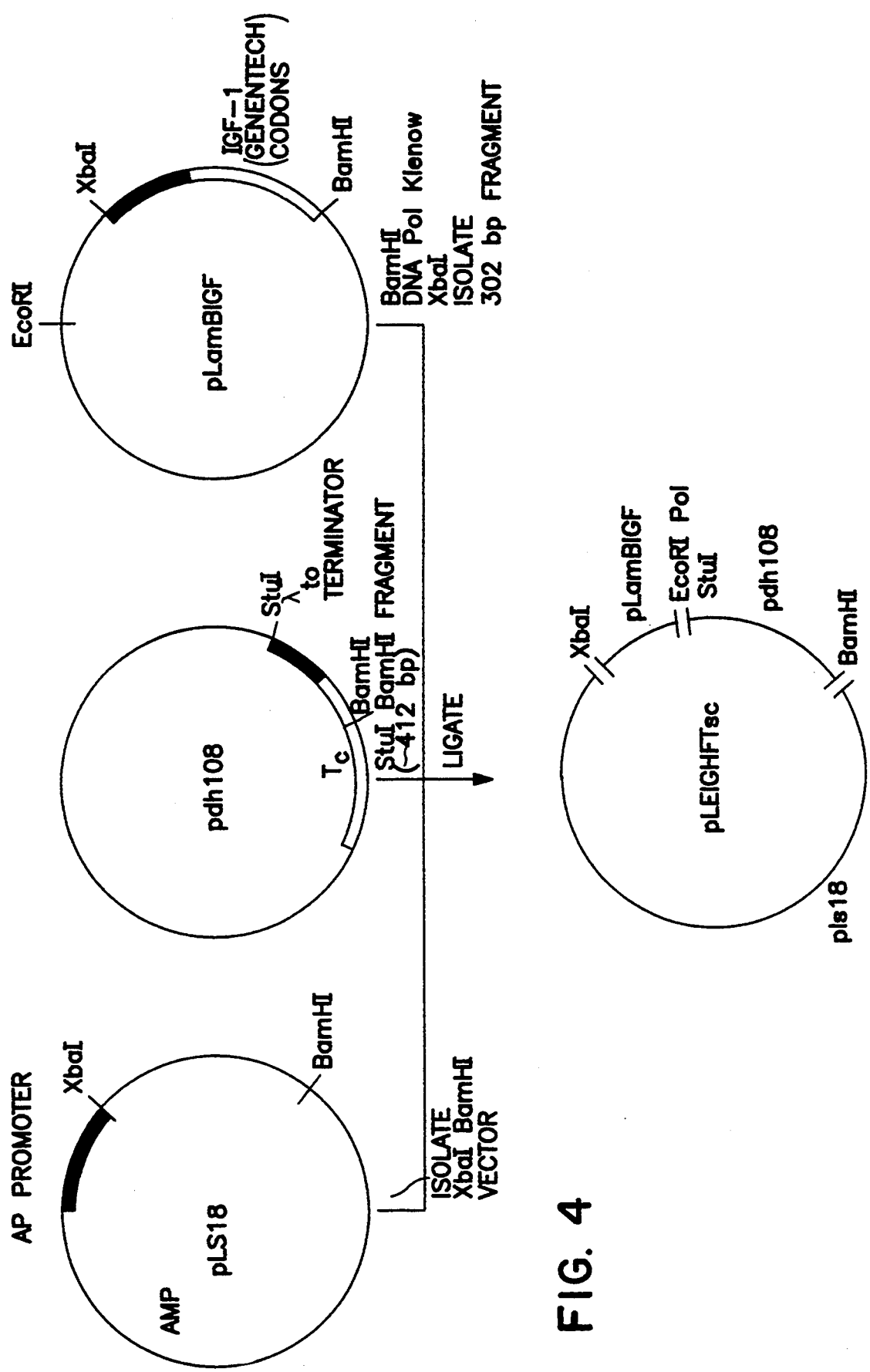
FIG. 4 depicts the construction of the intermediate plasmid pLBIGFTsc from pLamBIGF.

The XbaI-BamHI vector fragment was isolated from pLS18 as the first ligation fragment. The second part of the ligation was a 412-bp StuI-BamHI fragment from the plasmid pdH108-4 described above. The third part of the ligation was prepared by an EcoRI digest of pLamBIGF, followed by treatment with DNA polymerase Klenow fragment, followed by a XbaI digest. The resultant 302-bp fragment was isolated. These three fragments were ligated to yield pLBIGFTsc, as shown in FIG. 4.

Step 3: pRanTsc

Figure 5:
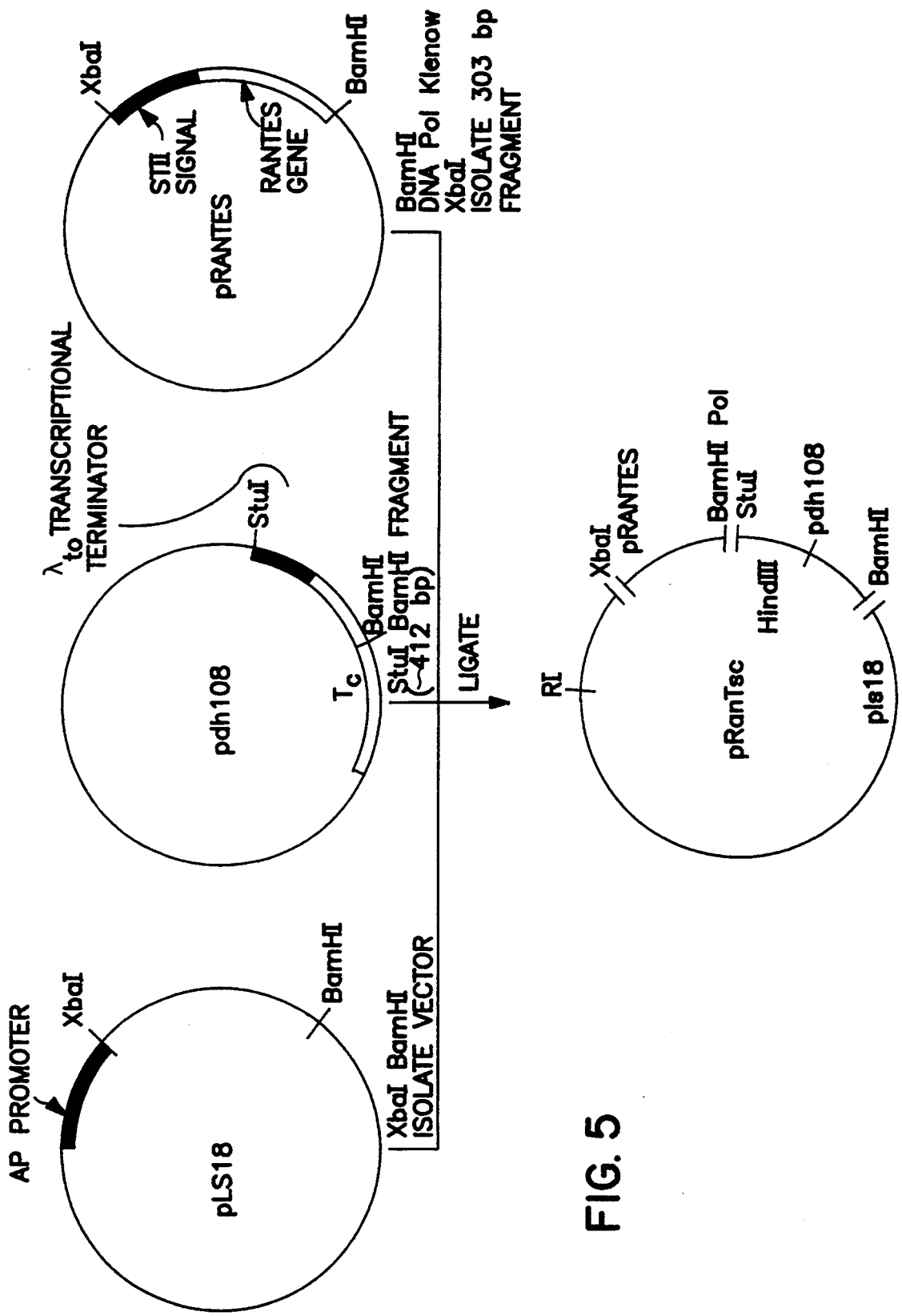
FIG. 5 depicts the construction of the intermediate plasmid pRanTsc used in the production of pBKIGF-2.

The XbaI-BamHI vector fragment from pLS18 was isolated as the first ligation fragment. The second part of the ligation was a 412-bp StuI-BamHI fragment from the plasmid pdH108-4 described above. The third part of the ligation was prepared from pRANTES. pRANTES is a pBR322-based plasmid containing a fragment of a XbaI linker followed by the STII signal, followed by the cDNA encoding RANTES [as published by Schall et al., *J. Immunol.*, 141: 1018 (1988)], followed by the BamHI linker. The third fragment was prepared by digestion of pRANTES with BamHI, followed by treatment with DNA polymerase Klenow fragment, followed by a XbaI digest. The resultant 303-bp fragment was isolated. These three fragments were ligated to yield pRanTsc, as shown in FIG. 5.

Step 4: pBKIGF-2

Figure 6:
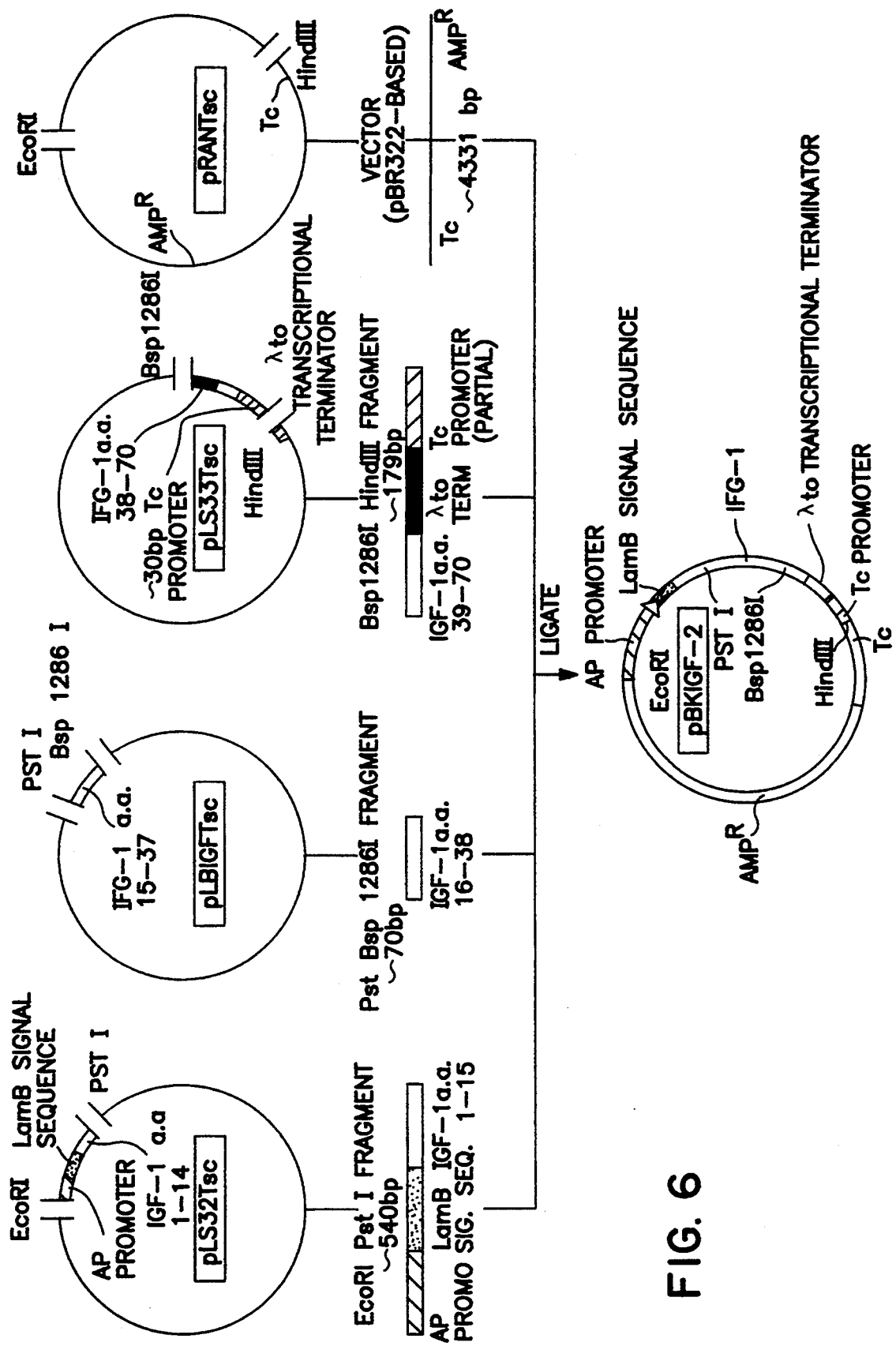
FIG. 6 depicts the construction of pBKIGF-2 from pLS32Tsc, pLBIGFTsc, pLS33Tsc, and pRanTsc.

As shown in FIG. 6, the EcoRI-PstI 540-bp fragment containing the alkaline phosphatase promoter, the lamB signal sequence, and DNA encoding the first 15 amino acids of IGF-I was excised from pLS32Tsc. The Pst-Bsp1286I fragment (~70 bp) containing DNA encoding amino acids 16-38 of IGF-I was excised from pLBIGFTsc. The Bsp1286I-HindIII (~179-bp) fragment containing DNA encoding amino acids 39-70 of IGF-I, the lambda terminator, and the Tc promoter was excised from pLS33Tsc. Finally, the EcoRI-HindIII ~4331-bp vector fragment (pBR322-based) was excised from pRanTsc. These four fragments were ligated to give pBKIGF-2, which contains the AP promoter, the lamB signal sequence, the DNA encoding the entire IGF-I protein, the transcriptional terminator, the Tc promoter, and the tetracycline and ampicillin resistance markers.

Step 5: pBKIGF-2A pBKIGF-2 was digested with PstI and ClaI and the ~245-bp fragment was isolated. This contains amino acids 16-70 of IGF-I and the lambda $t_o$ terminator. pLBIGFTsc was digested with NcoI and ClaI and the vector fragment was isolated. This vector fragment contains the AP promoter, the lamB signal, and the Tet$^r$ gene. These two fragments were ligated to a piece of synthetic DNA that replaces the 5' end of IGF-I DNA from NcoI to PstI with synthetically derived codons as follows:

5'-CATGGCC GGT CCC GAA ACT CTG TGC
GGT GCT GAA CTG GTT GAC GCT CTG
CA-3'

3'-CGG CCA GGG CTT TGA GAC ACG CCA
CGA CTT GAC CAA CTG CGA G-5'

Figure 7:
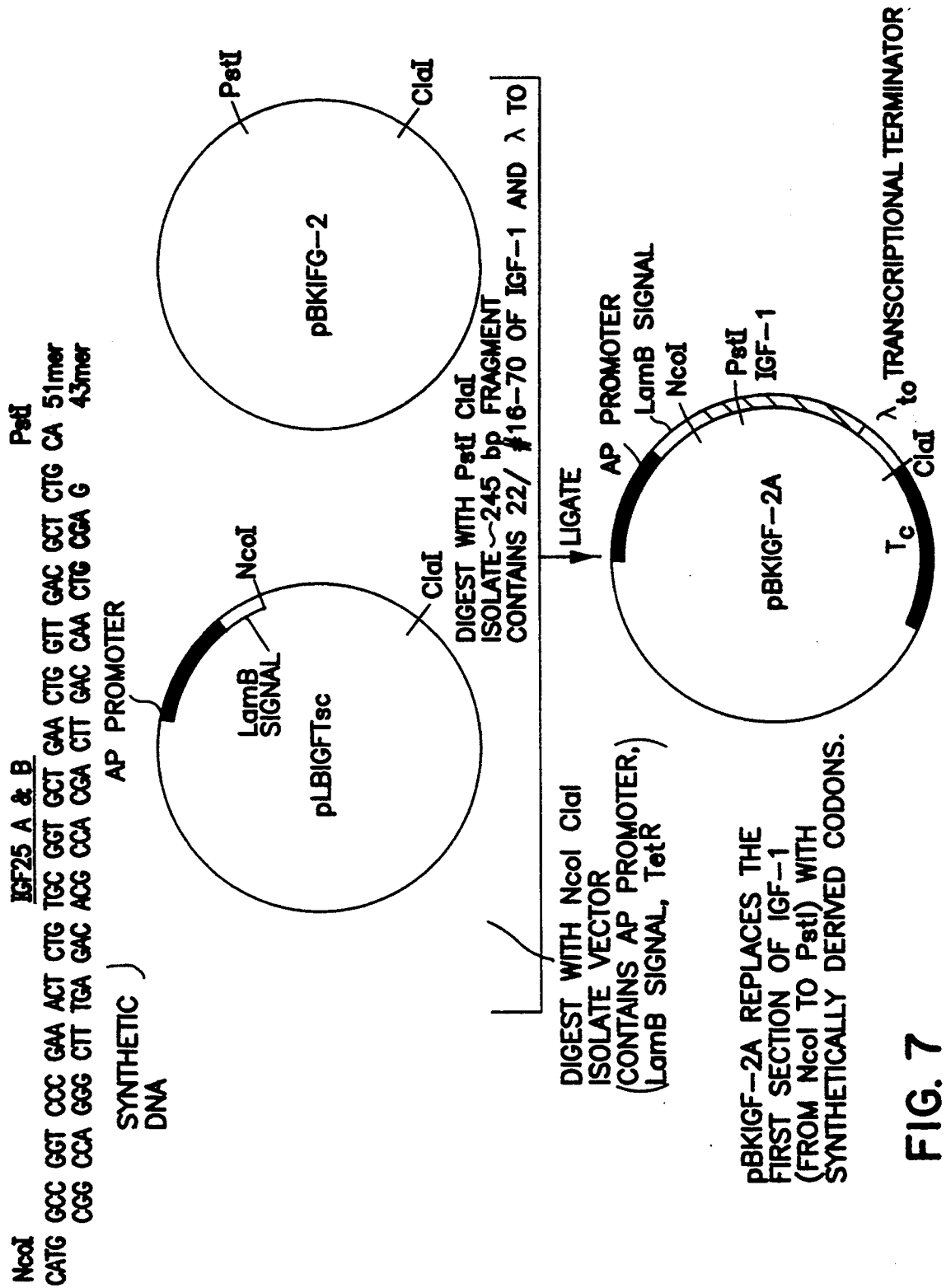
FIG. 7 depicts the construction of pBKIGF-2A, used to prepare pBKIGF-2B, from pLBIGFTsc, pBKIGF-2, and a piece of synthetic DNA (SEQ. ID NOS. 4 and 5).

(SEQ. ID NOS. 4 and 5, respectively).
The resulting plasmid was designated pBKIGF-2A. The construction is shown in FIG. 7.

Step 6: pLamBRan

This plasmid was prepared by digesting pLS33LamB with NcoI and BamHI and the vector fragment was isolated. pLS33LamB is a plasmid made from pBR322 into which was inserted the AP promoter, the lamB signal, and the IGF-I gene. BamHI cuts in the Tc portion of the plasmid and NcoI cuts at the 5' end of the IGF-I gene. The second fragment was generated by digesting pRANTES with BsaJI and BamHI and isolating the resultant ~200-bp fragment. The third fragment was a piece of synthetic DNA to link the RANTES gene with the signal sequence from NcoI to BsaJI. This synthetic DNA has the sequence:

| NcoI | BsaJI |
|---|---|
| 5'-CATGGCCTCCCCATATTC-3' | |
| 3'-CGGAGGGGTATAAGGAGC-5' | |

Figure 8:
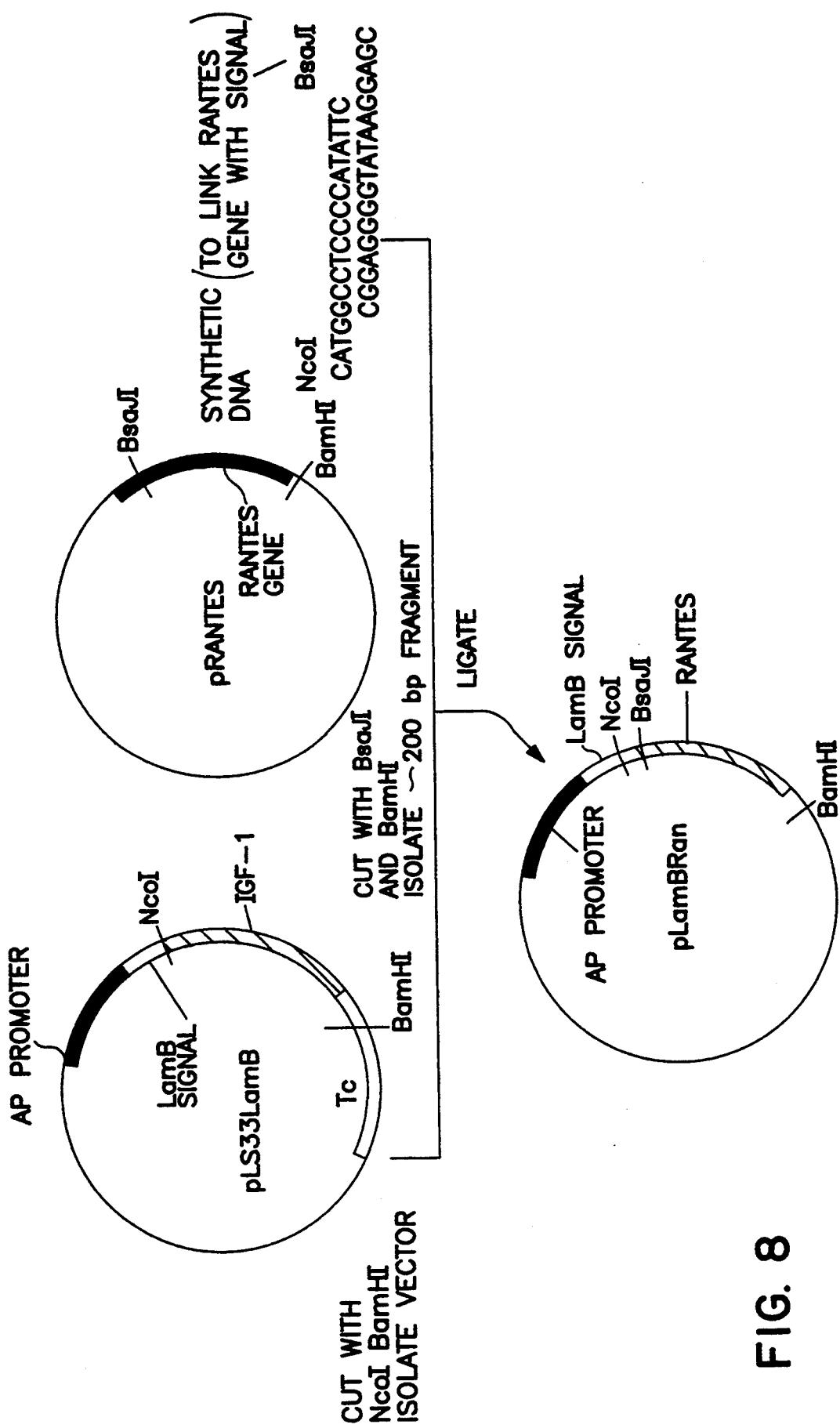
FIG. 8 depicts the construction of pLamBRan, used to prepare pBKIGF-2B, from pLS33LamB, pRANTES and a piece of synthetic DNA (SEQ. ID NOS. 6 and 7).

(SEQ. ID NOS. 6 and 7, respectively).
The resulting vector was named pLamBRan, and its construction is shown in FIG. 8.

Step 7: pBKIGF-2B

Figure 9:
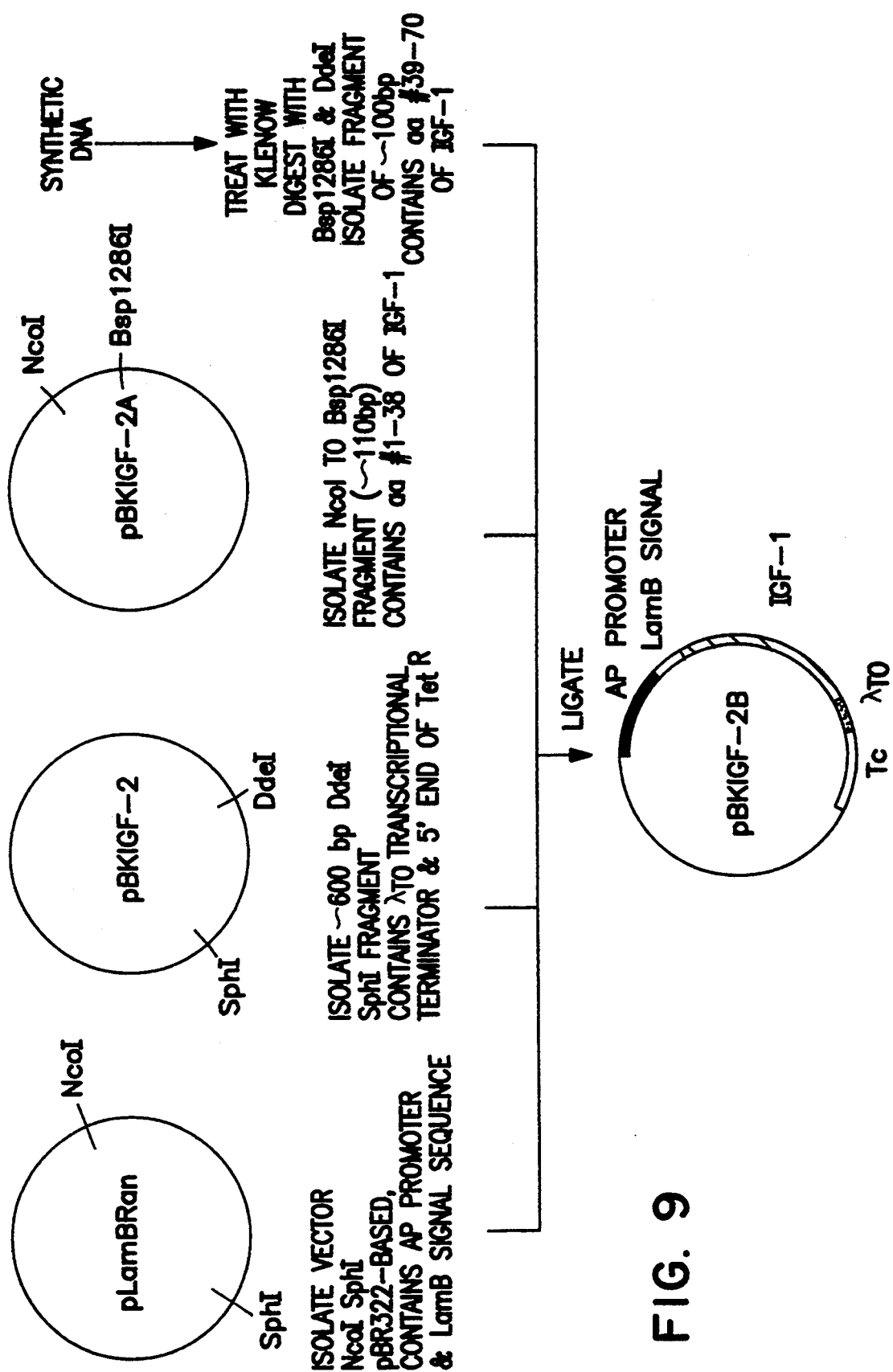
FIG. 9 depicts the construction of expression vector pBKIGF-2B from pBKIGF-2, pBKIGF-2A, pLamBRan, and a piece of synthetic DNA (SEQ. ID NOS. 8 and 9).

The construction of this plasmid is shown in FIG. 9. pLamBRan was digested with NcoI and SphI and the vector fragment was isolated containing the promoter and signal sequences. pBKIGF-2 was digested with DdeI and SphI and the ~600-bp fragment was isolated containing the lambda transcriptional terminator and the 5' end of the Tet$^R$ gene. pBKIGF-2A was digested with NcoI and Bsp1286I and the ~110-bp fragment was isolated containing the DNA encoding amino acids 1-38 of IGF-I. These three fragments were ligated together with synthetic DNA encoding amino acids 39-70 of IGF-I to yield pBKIGF-2B. This synthetic linker has the sequence:

5'-TCGTCGTGCTCCC CAG ACT GGT ATT
GTT GAC GAA TGC TGC TTT CGT TCT
TGC GAC CTG CGT CGT CTG-3'     (SEQ. ID NO. 8)

3'-AGA ACG CTG GAC GCA GCA GAC CTT
TAC ATA ACG CGA GGG GAC TTT GGG
CGATTTAGACGAATCTTCGAGG-5' (SEQ. ID NO. 9)

C. Fermentation i. Transformation

Competent *E. coli* 27C7 cells were transformed with pBKIGF-2B by standard transformation techniques. Transformants were selected and purified on LB plates containing 20 mg/L tetracycline. This medium had the following composition: 10 g/L Bacto-Tryptone, 5 g/L yeast extract, 10 g/L sodium chloride, and 20 mg/L tetracycline-HCl.

ii. Fermentation Inoculum

A 10-L fermentor inoculum was prepared by first inoculating a two-liter shake flask containing approximately 500 mL of sterile LB medium containing tetracycline with freshly thawed 1-2 mL of stock culture. This flask was incubated at 35°-39° C. for 8 hours and transferred into a 10-liter fermentor containing the production medium in the range of that described in Section C(iii) of this Example. The 10-liter fermentor inoculum was incubated at 35°-39° C. at pH 7.1-7.5 for 6-12 hours. The agitation rate was set at 650-1000 rpm and the aeration rate at 0.7-1.5 volumes of air per volume of culture per minute. The inoculum was then aseptically transferred to a 1000-L fermentation vessel wherein glucose is introduced from the bottom.

The 10-L inoculum was grown like the 500-mL shake flask cultivation to mid-exponential phase (batch cultivation). All the glucose was added to the 10-L fermentor at the start of the fermentation. Only the 1000-L fermentation utilized glucose feeding.

iii. Fermentation Procedure

The 1000-L vessel initially contained 600-800 liters of fermentation medium composed as follows:

| Ingredient | Quantity/Liter |
| --- | --- |
| glucose* | 250-350 g |
| ammonium sulfate | 3-8 g |
| ammonium hydroxide | as required to control pH 7.1 to 7.5 |
| sodium phosphate, monobasic dihydrate | 1-2 g |
| potassium phosphate, dibasic | 2-4 g |
| sodium citrate, dihydrate | 0.5-1.5 g |
| potassium chloride | 1-2.5 g |
| 25% Pluronic Polyol L61 | 0.1-0.2 mL initially and as needed to control foaming |
| magnesium sulfate, heptahydrate | 1-3 g |
| tetracycline HCl | 5-20 mg |
| yeast extract** | 5-20 g |
| NZ amine AS** | 5-25 g |
| isoleucine | 0-10 g |
| methionine** | 0-1 g |
| ferric chloride, heptahydrate | 10-30 mg |
| zinc sulfate, heptahydrate | 2-5 mg |
| cobalt chloride, hexahydrate | 2-5 mg |
| sodium molybdate, dihydrate | 2-5 mg |
| cupric sulfate, pentahydrate | 2-5 mg |
| boric acid | 0.5-2 mg |
| manganese sulfate, monohydrate | 1-3 mg |

*1-5 g/L of glucose was added to the culture initially. The remainder was fed to the culture over the course of the fermentation.
**Yeast extract, NZ amine AS, and methionine can be added initially and/or fed throughout the fermentation.

The fermentation process was performed at 35°-39° C. at pH 7.1-7.5 for 24-48 hours. The agitation rate was set at 200 rpm and the aeration rate at 0.7-1.5 volumes of air per volume of culture per minute. Production of IGF-I occurred after the phosphate in the medium was depleted. This procedure resulted in fermentation broth containing approximately 18% packed cell volume and over 3 g/L IGF-I, which was principally in the periplasmic space with low levels in the extracellular medium.

D. In-situ Solubilization

At the end of fermentation, all feeds and controllers, with the exception of temperature, were turned off. Temperature control was maintained at 37° C. The sparge was shut off and fermentor back pressure was released. The broth volume was drained to 1200 L and the agitation rate was lowered from 200 rpm to 150 rpm. The sparge lines and fermentor headspace were then flushed with nitrogen gas, first at a rate of 150 Lpm for 1 minute, then at 50 Lpm for the remainder of the procedure. A 220-L slurry containing 174 kg of urea was then pumped rapidly into the fermentor, followed immediately by approximately 8 L of 50% (w/w) sodium hydroxide, sufficient to adjust the pH to 10.0. A 20-L solution containing 2.9 kg of dithiothreitol was then added and the pH was re-adjusted to 10.0 with approximately 3 additional liters of 50% sodium hydroxide. The batch was held with agitation at 37° C. for 60 minutes, after which it was cooled to 22° C. and transferred to a hold tank for aqueous two-phase extraction. Assays by reversed-phase HPLC showed that the initial titer of IGF-I was 3.8 g/L, and after solubilization IGF-I was quantitatively released from the cells.

E. Aqueous Two-Phase Liquid-Liquid Extraction

The batch temperature was maintained at 22° C. and the tank headspace was flushed with nitrogen. To the treated broth, having a volume of 1450 L, was added 250 kg of PEG-8000 and 90 kg of sodium sulfate. The batch was stirred for approximately 40 minutes. Centrifugation and analysis of samples showed that the phase-volume ratio (Kv) stabilized at 2.6 and the IGF-I distribution coefficient (Kc) was 8.5. The batch was separated using a Westfalia SB-7 separator, yielding approximately 1300 L of light phase and 550 L of heavy phase. Assays by reversed-phase HPLC showed that the isolated light phase contained approximately 88% of the IGF-I in the initial 1450 L of treated broth. The light phase was held under nitrogen and the heavy phase was discarded.

F. Precipitation of IGF-I

Approximately 36 L of 2M phosphoric acid was added to the light phase to adjust the pH to 7.0 at 22° C. The batch was held for approximately 8 hours with gently mixing, at which point assay by reversed-phase HPLC showed that approximately 96% of the IGF-I had precipitated. The pellet was then collected using a Westfalia SB-7 clarifier. The mass of the pellet slurry was approximately 88 kg.

G. Refolding

An aliquot of the pellet slurry, having a mass of 17.6 kg, was dissolved by adding sufficient solid urea to bring the final concentration to 2M, by adding sufficient dithiothreitol to bring the concentration to 10 mM, and by adjusting the pH to 10.0 with 50% (w/w) sodium hydroxide. It was then added to 700 L of folding buffer having a composition of 2M urea, 1M sodium chloride, 19% (v/v) ethanol, 20 mM glycine, 0.5 µM copper, pH 10.5. The final concentration of dithiothreitol was then adjusted to 1 mM. Folding was carried out at 22° C. with gentle mixing by sparging in oxygen gas at 280 mL/minute. The progress of folding was monitored by reversed-phase HPLC. After approximately 3 hours, folding was terminated by cessation of oxygen sparging and by titrating the batch to pH 3.5 with approximately 1.6 L of reagent phosphoric acid. Assay by reversed-phase HPLC showed that the yield of properly folded IGF-I monomer was 50% of the total IGF-I polypeptide in the folding mixture.

H. Acid C-4 Chromatography

In this step, folded IGF-I monomer was separated from aggregated IGF-I and other hydrophobic impurities which were present in the folding mixture. This separation was achieved using a wide-pore, reversed-phase resin and the entire operation can be performed in conventional low-pressure glass columns.

Step 1. Column Preparation

One part of dry packing (Bakerbond C-4, 40 μm/275 Å, obtained from J. T. Baker) was resuspended in 5 parts of isopropanol (twice) to remove fines. A slurry of approximately 1 part resin to 2 parts isopropanol was transferred to an appropriately sized glass column. The bed was equilibrated with isopropanol until a constant bed length was obtained. Then, the top flow adaptor was positioned above the packed bed and the column was equilibrated with 2 column volumes (CV) of a buffer containing 50% isopropanol/0.5M glycine, pH 10. To prevent column degassing, a positive pressure across the packed bed of approximately 15 psig was maintained by adjusting the column outlet valve whenever fluid was passing through the column. Immediately after this step, the column was washed with 4 CV of 40% ethanol/50 mM NaCl/50 mM acetic acid, pH 3. The column was now ready for use. A packed bed height of approximately 25 cm in a 30-cm diameter column was routinely used (approximately 18-L bed volume).

Step 2. Sample Preparation and Loading

Approximately 700 L of the acidified folding pool was clarified by passing it through an ultrafiltration membrane (300,000 dalton molecular weight cutoff). This material was loaded directly onto the acid C-4 column that was previously equilibrated with 3 CV of acid folding buffer (2M urea, 1M NaCl, 20% (v/v) ethanol, 20 mM glycine, pH 3.5) at a rate of up to 20 CV/hr. Analysis of the column effluent by HPLC or SDS-PAGE showed that no IGF-I was lost during loading.

Step 3. Wash and Elution

After sample loading, the column was washed with approximately 3 CV of acid folding buffer until the absorbance (280 nm) returned to baseline. Then, 3 CV of 50 mM NaCl/50 mM acetic acid, pH 3.5, were passed through the column to remove excess salt, urea, and solvent.

The IGF-I which was bound to the column was eluted with a linear gradient of approximately 28–32% ethanol in 50 mM NaCl, 50 mM acetic acid, pH 3.5. A flow rate of approximately 3 CV/hr was used to deliver 6 CV of this gradient elution buffer. By RP-HPLC, 90–95% of the correctly folded IGF-I monomer was routinely recovered from the clarified folded pool. The distribution of IGF-I in this pool by RP-HPLC analysis was generally 15–25% misfolded, 2–5% oxidized, and 70–80% correctly folded monomer. By SDS-PAGE and protein blotting, the only proteins detected in the acid C-4 pool were IGF-I. It is significant to note that after elution, the C-4 resin was still very dark brown.

After elution of the IGF-I monomer, the column was regenerated using 2 CV of 50% isopropanol/0.5M glycine, pH 10, followed by 2 CV of 20% ethanol in 50 mM NaCl, 50 mM acetic acid, pH 3.5. After this regeneration step, the resin returned to its original, off-white color.

I. Cation-Exchange Chromatography

The pool from step H was loaded onto a column packed with a cation-exchange resin, in this case S-SEPHAROSE TM agarose Fast Flow TM (Pharmacia) medium, which had been previously equilibrated with 50 mM acetic acid, 50 mM NaCl, pH 3. The protein load to the column was approximately 20 mg IGF-I/mL bed volume. The column was washed sequentially with 3 CV of equilibration buffer, 4 CV of 50 mM Tris buffer, pH 8, and 1 CV of 10 mM citrate buffer, pH 6. At a pH just under the isoelectric point of IGF-I (8.45), the pH 8 Tris buffer washed off any remaining impurities, endotoxin contaminants, and metals. The IGF-I was eluted with 200 mM citrate buffer, pH 6. The column was regenerated with 0.5 N NaOH.

EXAMPLE II

In this example, using a 1000-L direct secretion fermentation, IGF-I is specifically eluted from a silica chromatography column.

A. Host Cell Strain

The host used to produce recombinant human IGF-I in the fermentation described in this example was a derivative of *E. coli* W3110, designated 27C7. The complete genotype of 27C7 is tonA ptr3 phoAΔE15 Δ(argF-lac)169 ΔdegP ΔompT kan$^r$ as found in WO 93/11240 published Jun. , 10, 1993, the disclosure of which is incorporated herein by reference. Strain 27C7 was deposited on Oct. 30, 1991 in the American Type Culture Collection as ATCC No. 55,244.

B. Expression Plasmid

The secretion plasmid pLS32Tsc used in this example contains the IGF-I gene. The transcriptional and translational sequences required for expression of the IGF-I gene in *E. coli* are provided by the alkaline phosphatase promoter and the trp Shine-Dalgarno sequence. The lambda $t_o$ transcriptional terminator is situated adjacent to the IGF-I termination codon. Secretion of the protein from the cytoplasm is directed by the lamB signal sequence or alternatively the STII signal sequence. The majority of IGF-I is found in the cell periplasmic space. Plasmid pLS32Tsc confers tetracycline resistance upon the transformed host.

Plasmid pLS32Tsc was constructed in several steps using as intermediate plasmids pLS32, pAPlamB, pLS321lamB, pLS33lamB, and pLS33Tsc as disclosed in detail in WO 93/11240, supra.

Transformants were obtained by standard transformation techniques and selected and purified on LB plates containing 20 mg/L tetracycline. This medium had the following composition: 10 g/L Bacto-Tryptone, 5 g/L yeast extract, 10 g/L sodium chloride, 20 mg/L tetracycline-HCl, and 15 g/L agar.

C. Fermentation

The fermentation process for producing IGF-I by the direct secretion method using *E. coli* 27C7/pLS32Tsc was performed in batches ranging from 10 to approximately 1000 liters. A shake flask was prepared by inoculating sterile LB broth containing 20 mg/L tetracycline with freshly thawed stock culture. The shake flask was incubated at 35°–39° C. at 50–200 rpm for 7–12 hours. The shake flask was used to inoculate a secondary inoculum culture grown in a 10-L fermentation vessel using production medium. The secondary inoculum was grown at 35°–39° C. until the optical density at 550 nm reached 20–35. This culture was then used to inoculate the 1000-L production broth. All inocula volumes were between 0.1% and 10% of the initial volume of media.

The composition of the medium is shown below. All medium components were sterilized by heat treatment or filtration.

| Ingredient | Quantity/L |
| --- | --- |
| Glucose* | 10–300 g |
| Ammonium Sulfate | 2–6 g |
| Sodium Phosphate, Monobasic Dihydrate | 1–5 g |
| Potassium Phosphate, Dibasic | 1–5 g |
| Sodium Citrate, Dihydrate | 0.5–5 g |
| Potassium Chloride | 0.5–5 g |
| Magnesium Sulfate, heptahydrate | 0.5–5 g |
| Pluronic Polyol, L61 | 0.1–2 mL |
| Ferric Chloride, Heptahydrate | 10–100 mg |
| Zinc Sulfate, Heptahydrate | 0.1–10 mg |
| Cobalt Chloride, Hexahydrate | 0.1–10 mg |
| Sodium Molybdate, Dihydrate | 0.1–10 mg |
| Cupric Sulfate, Pentahydrate | 0.1–10 mg |
| Boric Acid | 0.1–10 mg |
| Manganese Sulfate, Monohydrate | 0.1–10 mg |
| Tetracycline | 5–30 mg |
| Yeast Extract** | 5–15 g |
| NZ Amine AS** | 5–15 g |
| Methionine** | 0–5 g |
| Ammonium Hydroxide | as required to control pH |
| Sulfuric Acid | as required to control pH |

*A portion of the glucose was added to the medium initially, with the remainder being fed throughout the fermentation.
**These components can be fed throughout the fermentation.

The fermentation process was performed at 35°–39° C. and pH 7.0–7.8. The agitation rate was set at 200–800 rpm and the aeration rate at 0.5–2.0 volumes of air per volume of culture per minute. Production of IGF-I occurred when the phosphate in the medium was depleted. The fermentation was allowed to proceed for 25–35 hours, at which time the culture was chilled prior to harvest. The culture was inactivated by heat treatment using a continuous-flow apparatus with a flow rate of 15–25 L/min at 60°–70° C. or in-tank heat inactivation (10-L scale) at 60°–70° C. for 5–15 minutes. The heat-inactivated culture was centrifuged using a AX Alpha-laval centrifuge or equivalent and then the supernatant was clarified through a depth filter. The clarified fermentation broth was saved for further processing and the cells were discarded.

D. Silica Chromatography

Step 1. Column Preparation

One part of dry silica packing (grade 953 obtained from Davison Chemical Division of W. R. Grace) was resuspended in 5–10 parts of water (twice) to remove fines. A slurry of approximately 1 part resin to 2 parts water was transferred to an appropriately sized glass column. The bed was equilibrated with water until a constant bed length was obtained. Then, the top flow adaptor was positioned above the packed bed and the column was equilibrated with water at a flow rate of approximately 20 CV/hr. Once a stable baseline was achieved, the column was ready for use. A total of 3 CV of water was generally used to prepare a uniform packed bed. A packed bed height of approximately 20 cm in a 35-cm diameter column was routinely used (approximately 20-L bed volume).

Step 2. Sample Preparation and Loading

The clarified broth was loaded directly onto the silica column at a rate of approximately 10 CV/hr and a total of 50 CV was loaded. As judged by visual inspection, most of the colored material present in the broth passed through the column. Analysis of the column effluent by HPLC or SDS-PAGE showed that no IGF-I was lost during loading.

Step 3. Wash and Elution

After sample loading, the column was washed with 4 CV of 20 mM phosphate, pH 7, until the absorbance (280 nm) returned to baseline. The rate for the phosphate wash and all subsequent washes was approximately 3 CV/hr. Then, 4 CV of 20% ethanol in 20 mM phosphate, pH 7, were applied to the column. This removed a significant amount of protein contaminants relative to the small (about 5–10%) amount of IGF-I that was lost at this step.

The bulk of the IGF-I that was bound to the column was eluted by a buffer containing 20% ethanol and 1M NaCl in 0.1M phosphate, pH 7. By RP-HPLC analysis, 85–90% of the correctly folded IGF-I monomer was routinely recovered from the clarified fermentation broth. The distribution of IGF-I in this pool by HPLC analysis was generally 15–25% misfolded, 2–5% oxidized, and 30–40% correctly folded monomer. The remaining portion was primarily some aggregates of IGF-I. By SDS-PAGE, the major protein detected in the silica pool was IGF-I. It is significant to note that after elution, the silica column was still very dark brown. After elution of the IGF-I by the combination of ethanol and NaCl, the column was unpacked and the resin discarded after a single use.

E. Cation-Exchange Chromatography

The IGF-I was eluted from the silica column in 20 mM phosphate, 1M NaCl, 20% EtOH, pH 7. In order to facilitate binding of IGF-I to the cation-exchange column, the silica pool was diafiltered into a low ionic-strength buffer consisting of 20 mM sodium citrate, pH 6, using a 5000-dalton ultrafiltration system.

The diafiltered pool was then loaded onto a column packed with S-SEPHAROSE ™ agarose Fast Flow ™ (Pharmacia) medium, which had been previously equilibrated with the diafiltration buffer. The protein load to the column was approximately 10 mg IGF-I/mL bed volume. The column was washed sequentially with 5 CV of 20 mM acetic acid (pH ~3) and 4 CV of 50 mM Tris buffer, pH 8. Bound IGF-I was eluted with 20 mM sodium phosphate, 80 mM NaCl, pH 7. The column was regenerated with 0.5N NaOH.

EXAMPLE III

In this example, IGF-I is separated from its closely related variants by reversed-phase liquid chromatography in accordance with the invention herein.

A. Materials and Methods Used

The following chemicals were used: HPLC-grade ACN (J. T. Baker Inc., Phillipsburg, N.J.); HPLC-grade trifluoroacetic acid (TFA, Pierce Chemical Co., Rockford, Ill.); analytical-reagent grade NaCl; dibasic sodium phosphate; hydrochloric acid (HCl); sodium hydroxide (NaOH); and acetic acid (HAc) (Mallinckrodt Inc., Paris, Ky.). All aqueous mobile phases were made using purified water. pH adjustment was done with HCl or NaOH. All buffers were 0.2 μm-filtered prior to use.

Analytical RP-HPLC was performed on a 0.46×25 cm stainless steel column pre-packed with 5 μm, 300-Å, trifunctional, Vydac-C18 spherical silica (The Separations Group, Hesperia, Calif.). The development of preparative RP-HPLC methods was carried out using a 0.39×30 cm stainless-steel column pre-packed with 15 μm, 300-Å, mono-functional, Waters-C4 spherical silica (Millipore Co., Waters Chromatography Div., Milford, Mass.). The other preparative RP-HPLC columns that were evaluated include: Bakerbond-C4 (J. T. Baker), YMC-C8 (Yamamura Chemical Lab Inc., Morris Plains, N.J.); Kromasil-C8 (Eka Nobel AB, Surte Sweden); Amicon-C8 (Amicon, Danvers, Mass.); Impaq-C4 (PQ Corp., Valley Forge, Pa.); PLRP-S (Polymer Labs, Amherst, Mass.); and Eurosil-Bioselect (Paxxis, Belmont, Calif.). Pilot- and process-scale RP-HPLC was performed using the 15-$\mu$m, 300-Å, Waters-C4 media packed in 4.7×30 cm and 10×60 cm radial compression cartridges, respectively. In an alternative method, an axial compression preparative column from ProChrom was packed using bulk 15-$\mu$m Waters-C4 media.

Additional chemicals purchased for electrophoresis included: premixed Tris-glycine and Tris-tricine-SDS buffers (Novex, San Diego, Calif.); methanol (J. T. Baker, Phillipsburg, N.J.); Coomassie R-250 and Coomassie G-250 (Eastman Kodak Co., Rochester, N.Y.); sulfuric acid; glycerol (Mallinckrodt, Paris, Ky.); and trichloroacetic acid (Fisher Scientific, Fairlawn, N.J.).

The Vydac-C18 RP-HPLC analysis and the Waters-C4 preparative RP-HPLC methods development were both carried out on a Hewlett-Packard 1090 HPLC (Hewlett-Packard Co., North Hollywood, Calif.), equipped with a ternary gradient system and diode-array detector. The pilot-scale RP-HPLC was done using a Waters DeltaPrep 600-E controller, LC-3000 pumping system fitted with 180 mL/minute heads, and a 4.7×30 cm PrepPak radial compression module (RCM). The preparative RP-HPLC was accomplished using a Biotage KiloPrep-250 system (Biotage Inc., Charlottesville, Va.) and a 10×60 cm RCM.

Purity was assessed by 12% SDS-PAGE (Integrated Separation Systems, Hyde Park, Mass.), pH 3.5-9.5 isoelectric focusing (IEF) gels (Pharmacia LKB Biotechnology, Inc., Piscataway, N.J.), and analytical RP-HPLC using a 0.46×25 cm, 5 $\mu$m, 300-Å, Vydac-C18 column and Hewlett-Packard 1090 HPLC system. The SDS gels were run with Tris/tricine buffers [Schagger and Von Jagow, *Anal. Biochem.*, 166: 368 (1987)] and Coomassie-R250 stained. Andrews, *Electrophoresis*, Oxford University Press: New York, 1986. The low percentage polyacrylamide IEF gels could not be stained with silver or Coomassie R-250 because the IGF-I diffused out during the staining procedure. The gels were therefore stained in the absence of alcohol with Coomassie G-250. Neuhoff et al., *Electrophoresis*, 9: 255 (1988).

B. Background

A preparative-scale RP-HPLC step in the downstream processing of recombinant proteins is typically implemented late in the recovery scheme. This strategy is utilized to help maximize the efficiency of the separation and the column lifetime by removing the majority of the contaminants during previous purification steps. The RP-HPLC step for IGF-I was developed after the S-SEPHAROSE TM agarose step of Example II. The pool appeared to be homogeneous by SDS-PAGE and IEF analysis. However, RP-HPLC analysis on a 5-$\mu$m, 0.46×25 cm Vydac-C18 column using a 10–60% ACN/50-minute gradient at 22° C. revealed that other species were present (FIG. 10A). The expanded chromatogram (FIG. 10A, inset) showed two major peaks and some minor peaks. These minor, later-eluting peaks were immunoreactive to antibodies directed against IGF-I and appeared to be sequential multimeric species of IGF-I by immuno-blot analysis.

With the use of the same column at elevated temperature (50° C.), an isocratic separation baseline resolved the mixture into its four respective constituents (FIG. 10B). Canova-Davis et al., *Biochem. J.*, 285: 207 (1992). N-terminal sequence, peptide mapping, RP-HPLC, and mass-spectrometry analysis were performed on the four collected peaks that identified them as rhIGF-I, a methionine-sulfoxide variant, a misfolded form, and the respective misfolded-methionine-sulfoxide form. These results are consistent with those previously reported by Forsberg et al., *Biochem. J.*, 271: 357 (1990) and Raschdorf et al., *Biomedical and Environmental Mass Spectroscopy*, 16: 3-8 (1988).

Figure 11:
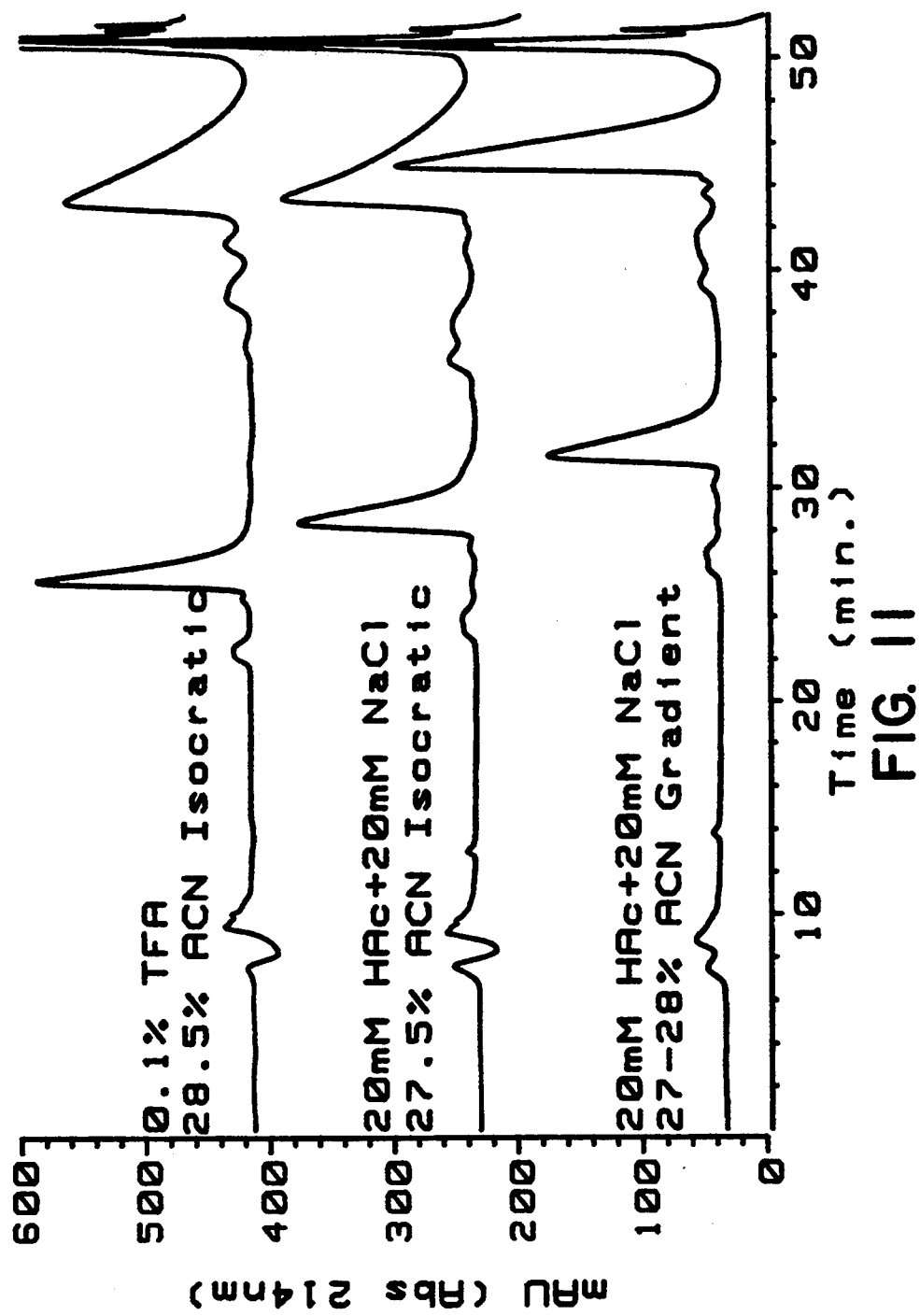
FIG. 11 shows counter-ion substitution and gradient effect, wherein the RP-HPLC chromatography was performed on a 5-μm Vydac-C18 column at 0.5 mL/minute, 50° C., either isocratically at 28.5% ACN/0.1% TFA (upper trace); isocratically at 27.5% ACN, 20 mM acetic acid, 20 mM NaCl (middle trace); or with acetic acid/NaCl using a shallow 27–28% ACN/40-minute gradient (lower trace).

The TFA counter-ion used in the analytical separation appeared to form a tight ion-pair with the product and was difficult to remove in subsequent process steps. This strong ion-pair interaction had been previously observed from synthetic peptides. Gabriel, *Int. J. Peptide Protein Res.*, 30: 40 (1987). A similar separation to 0.1 TFA, 28.5% ACN was achieved on the 5-$\mu$m Vydac-C18 column by using a low ionic strength acetate/halide pH 3 buffer (20 mM HAc, 20 mM NaCl) in 27.5% ACN (FIG. 11). The beneficial ion-pairing effects of NaCl in RP-HPLC have been previously reported in O'Hare and Nice, *J. Chromatogr.*, 171: 209 (1979). HAc or NaCl levels higher than 20 mM showed no further increase in resolution. The retention times were stabilized by changing the elution conditions from isocratic to a very shallow linear gradient, 27-28% ACN over 40 minutes.

C. Results

Figure 12A:
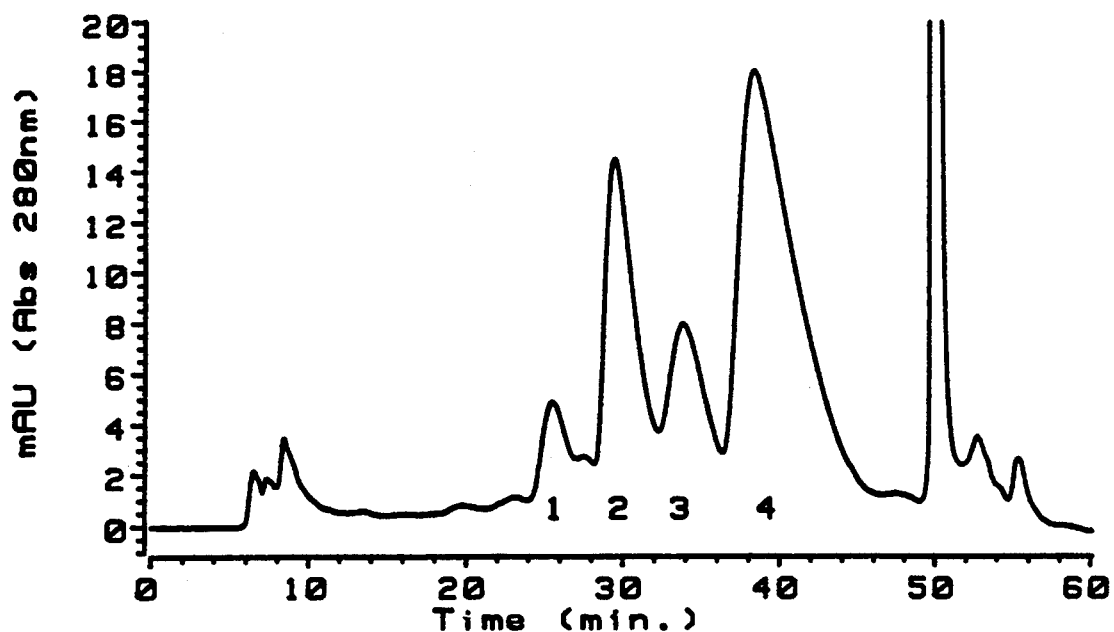
FIGS. 12A, 12B, and 12C are preparative RP-HPLC evaluations of the acetate buffer, pH 3, mobile phase.
Figure 12B:
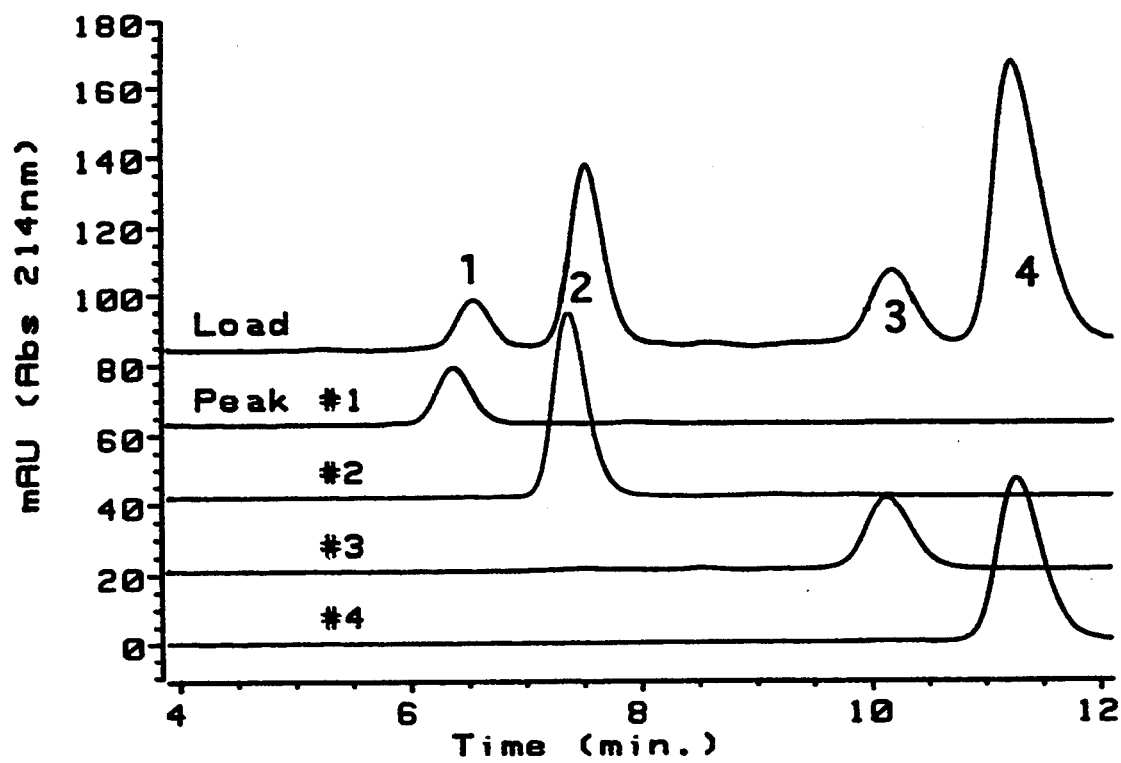

The acetate buffer mobile phase developed on the 5-$\mu$m Vydac-C18 column was adapted to a 15-$\mu$m Waters-C4 preparative medium packed in a 0.39×30 cm column (FIG. 12A). With use of the acetate buffer at 50° C., four peak fractions were collected during a shallow gradient elution, 27-28% ACN over 40 minutes. Fractions 1-4 were analyzed on the Vydac-C18 column as described above with the following modifications. Analytical through-put was increased by developing a rapid, near-isocratic (27-28% ACN with 0.1% TFA) method wherein the flow rate was increased from 0.5 to 2 mL/minute. The gradient volume was kept constant by shortening the duration from 40 to 10 minutes. Analysis of the peak fractions confirmed that the elution order of the IGF-I species using the acetate buffer was identical to the order with TFA (FIG. 12B).

Figure 12C:
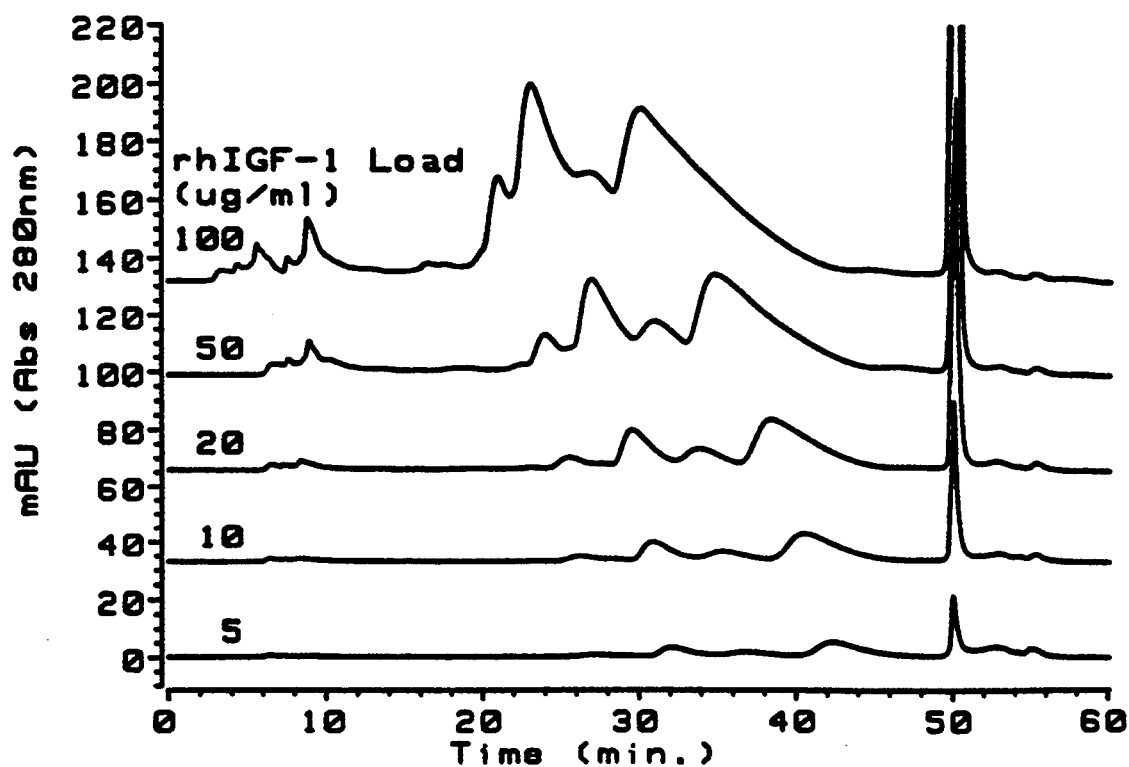

When the capacity of the C4 column using the acetate buffer mobile phase was evaluated, the non-linear profile became apparent. Even moderate loading (50 $\mu$g of rhIGF-I/mL bed volume) caused a loss in resolution between the product and the leading edge variants (FIG. 12C).

After the analytical method was transferred to a preparative medium, the selectivity of the mobile phase was investigated to enhance resolution, which would ultimately translate to higher effective capacity of well resolved rhIGF-I. A three-dimensional set of conditions was established within the framework of the following parameters: pH (3, 5, and 7), buffer concentration (20 and 100 mM), and temperature (22° and 50° C.). For this screen the solvent used was ACN and the counter-ions used were sodium, chloride, phosphate, and acetate.

Figure 13A:
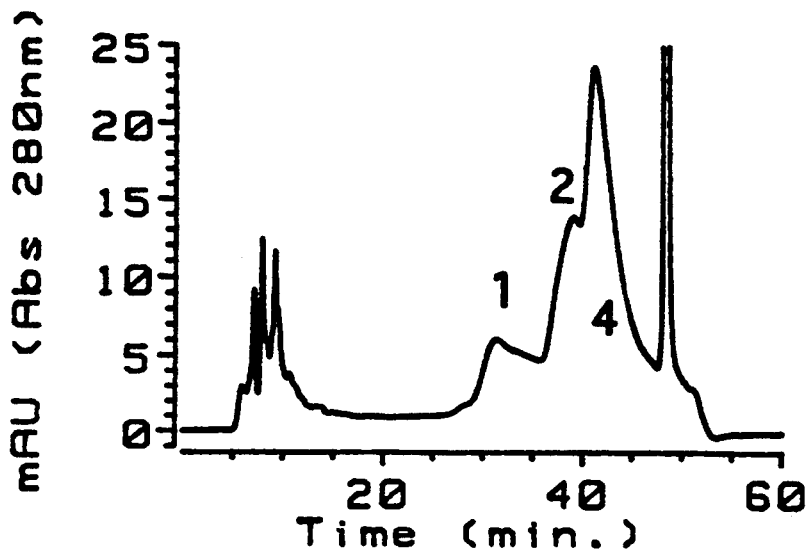
FIGS. 13A–F show the effect of pH and ionic strength, wherein the RP-HPLC chromatography was performed on an analytical size, 0.39×30 cm, 15-μm Water-C4 column equilibrated in 10% ACN and the respective counter-ion. The percent ACN was ramped in 1 minute to the initial gradient condition. The solvent strength was independently modified such that the rhIGF-I would elute during a near-isocratic 1% ACN/40-minute gradient at 0.7 mL/minute. The load level was maintained at 20 μg rhIGF-I/mL bed volume. The four predominant rhIGF-I species are labeled on the chromatogram: (1) methionine-sulfoxide/misfolded (MS-MF), (2) misfolded (MF), (3) methionine-sulfoxide (MS) and (4) rhIGF-I.
Figure 13B:
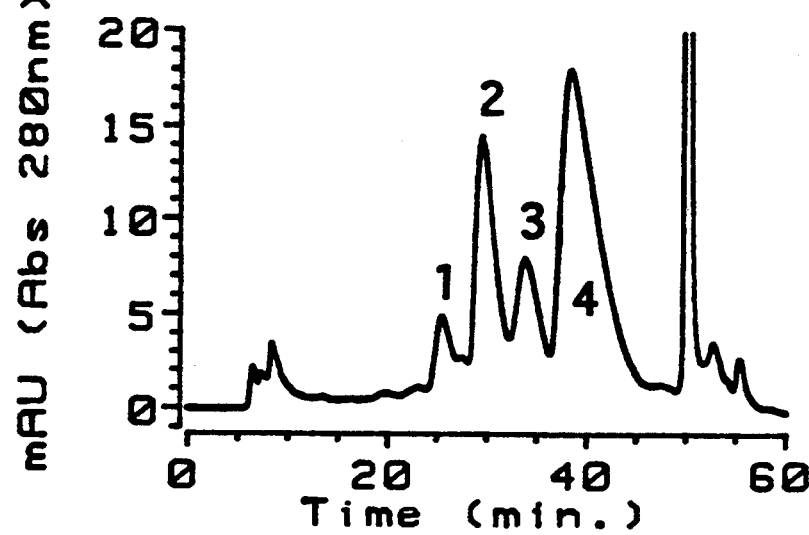
Figure 13C:
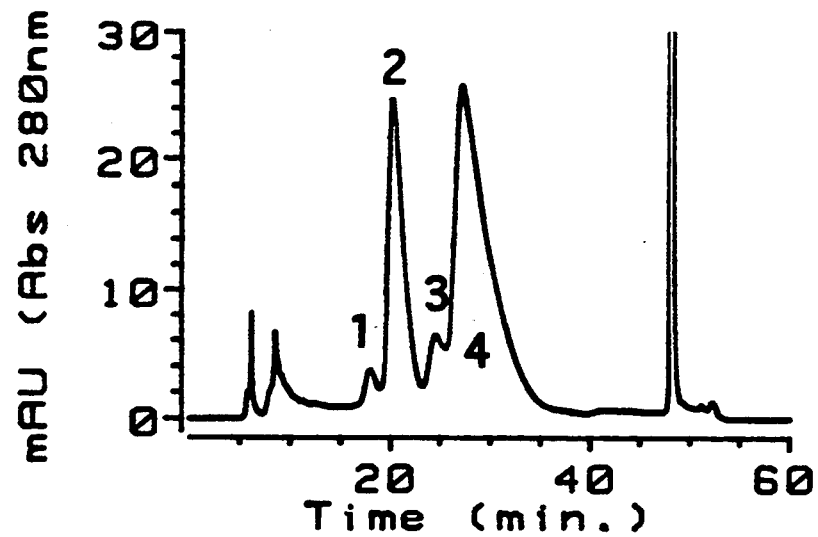

A 15-$\mu$m Waters-C4 column was equilibrated and loaded at 10% ACN for each mobile phase counter-ion condition, then ramped over one minute to the initial gradient condition. The solvent level was adjusted such that the IGF-I would elute during a 1% ACN gradient over 40 minutes. Low load levels (20 μg rhIGF-I/mL bed volume) were used throughout the evaluation to allow easy peak identification. Conducting the acetate buffer mobile phase Waters-C4 chromatography at 50° C. rather than 22° C. resulted in a dramatic peak sharpening (FIG. 13A-B). Since the higher temperature effects appeared generally beneficial, the 50° C. condition was maintained in all subsequent experiments. Concerning product stability, material generated at the higher temperature was biologically active. However, activity may be compromised at temperatures higher than 50° C. Changing the counter-ion from 20 mM acetate buffer (HAc/NaCl) to 20 mM phosphate buffer ($Na_2HPO_4$/HCl) while maintaining the pH at 3 had no major effect on resolution (FIG. 13C).

Figure 13D:
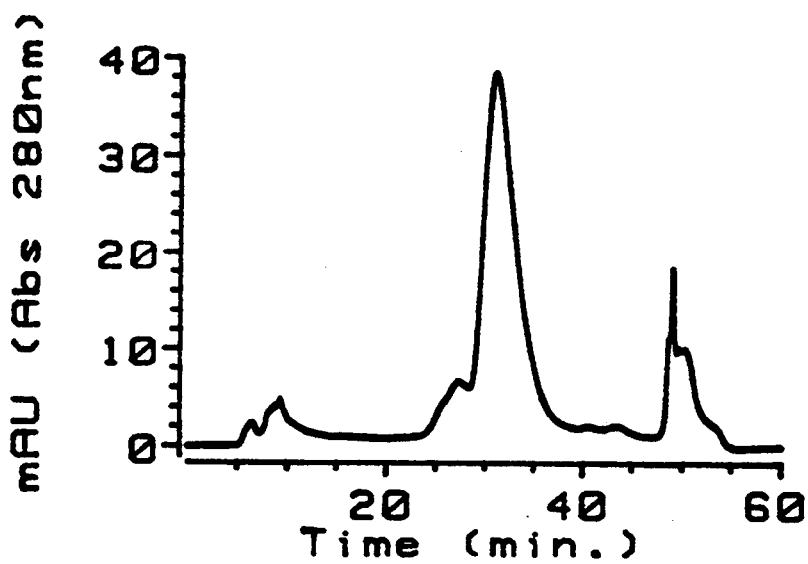
Figure 13E:
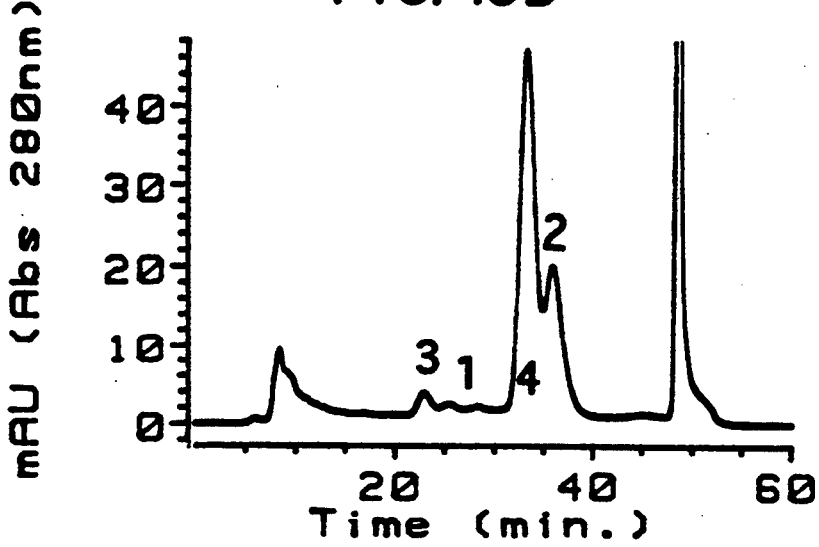
Figure 13F:
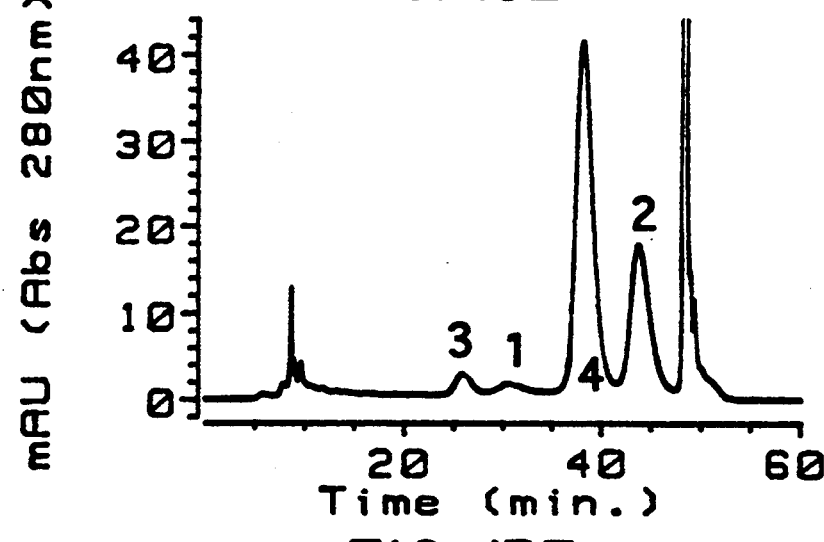

Increasing the pH from 3 to 5 using acetate buffer caused all four species to co-elute (FIG. 13D). However, a significant change in selectivity resulting in a further shift in both relative retention time and elution order of the four rhIGF-I variants occurred with an increase in the pH using 20 mM phosphate buffer, adjusted to pH 7 with HCl (FIG. 13E). Based on peak area, it was shown that the misfolded peak eluted after the main rhIGF-I peak, and the methionine-sulfoxide peak shifted from the leading edge of the product to the beginning of the gradient. The gradient conditions necessary for elution changed from 26-27% (pH 3) to 23-24% ACN (pH 7). The preferred conditions were achieved by raising the buffer concentration from 20 to 100 mM phosphate (FIG. 13F). Enhanced resolution correlated with an increase in peak symmetry. See Table 1. A similar separation was achieved when 100 mM potassium phosphate was used.

TABLE 1

Effects of pH and Buffer Concentration on Resolution and Peak Symmetry

| Counter Ion | pH | Buffer Conc. [mM] | Temp. °C. | Main As | Main/Met Rs | Main/Mis Rs |
|---|---|---|---|---|---|---|
| HAc + NaCl | 3 | 20 | 22 | 0.64 | * | 0.28 |
| HAc + NaCl | 3 | 20 | 50 | 0.37 | 0.65 | 1.51 |
| $Na_2HPO_4$ | 3 | 20 | 50 | 0.29 | 0.47 | 1.39 |
| HAc + NaCl | 5 | 20 | 50 | * | * | * |
| $Na_2HPO_4$ | 7 | 20 | 50 | 0.70 | 2.97 | 0.74 |
| $Na_2HPO_4$ | 7 | 100 | 50 | 0.78 | 3.48 | 1.51 |

*peaks overlap.
Main Peak Symmetry [Nice et al., supra], As = B/A.
A,B = Half peak width from vertical line from peak apex.
Resolution, Rs = [1.18 ($Rt_2-Rt_1$)]/($w_2 + w_1$)
Rt = Retention time, w = Peak width at half peak height.
Main/Met: Rs between main IGF-I peak and met-sulfoxide peak.
Main/Mis: Rs between main IGF-I peak and misfolded peak.

Figure 14C:
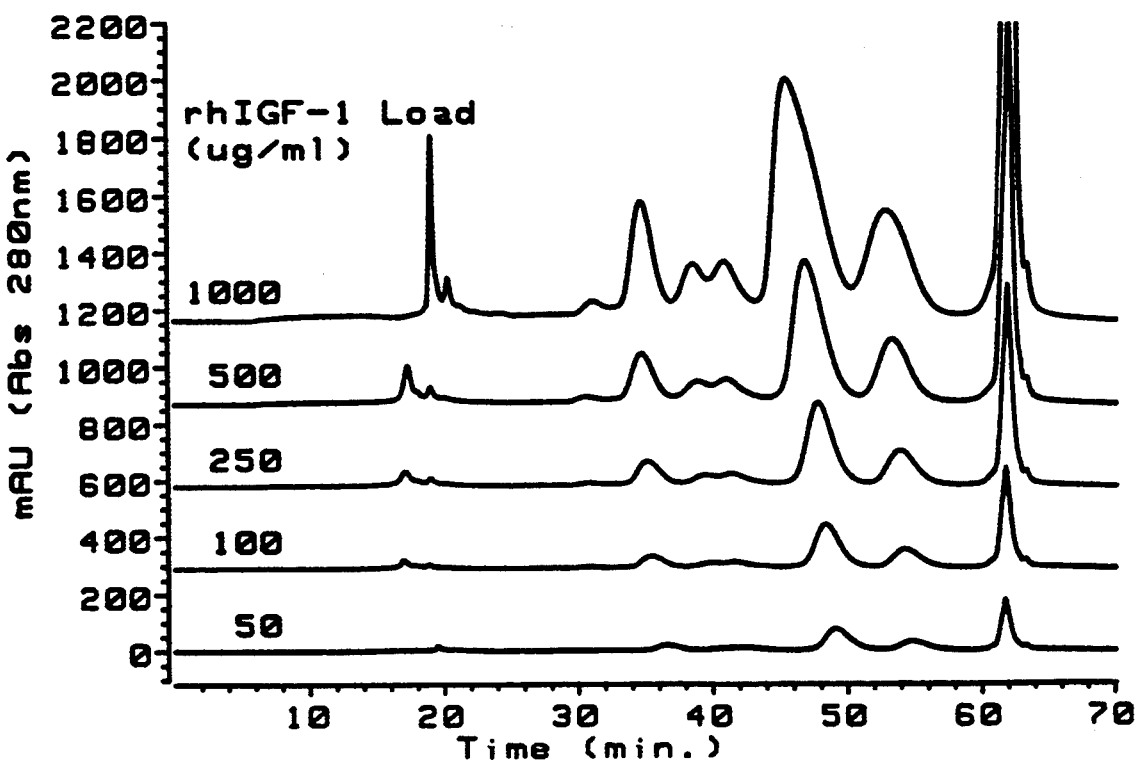
FIGS. 14A, 14B, and 14C are preparative RP-HPLC evaluations of the 100 mM phosphate buffer, pH 7, mobile phase.
Figure 14A:
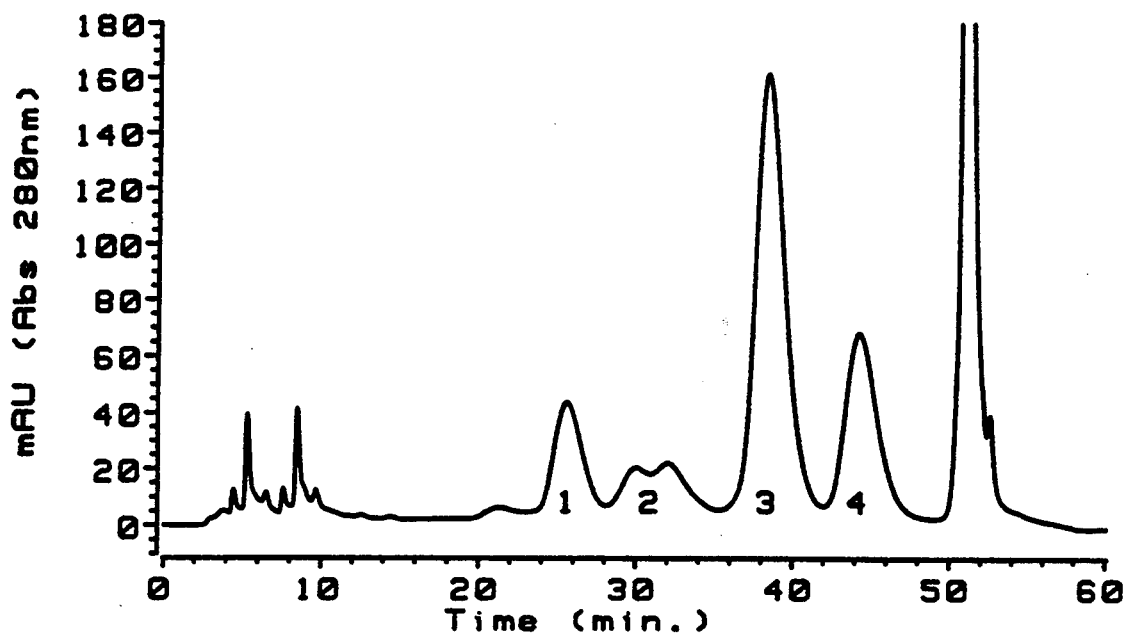
Figure 14B:
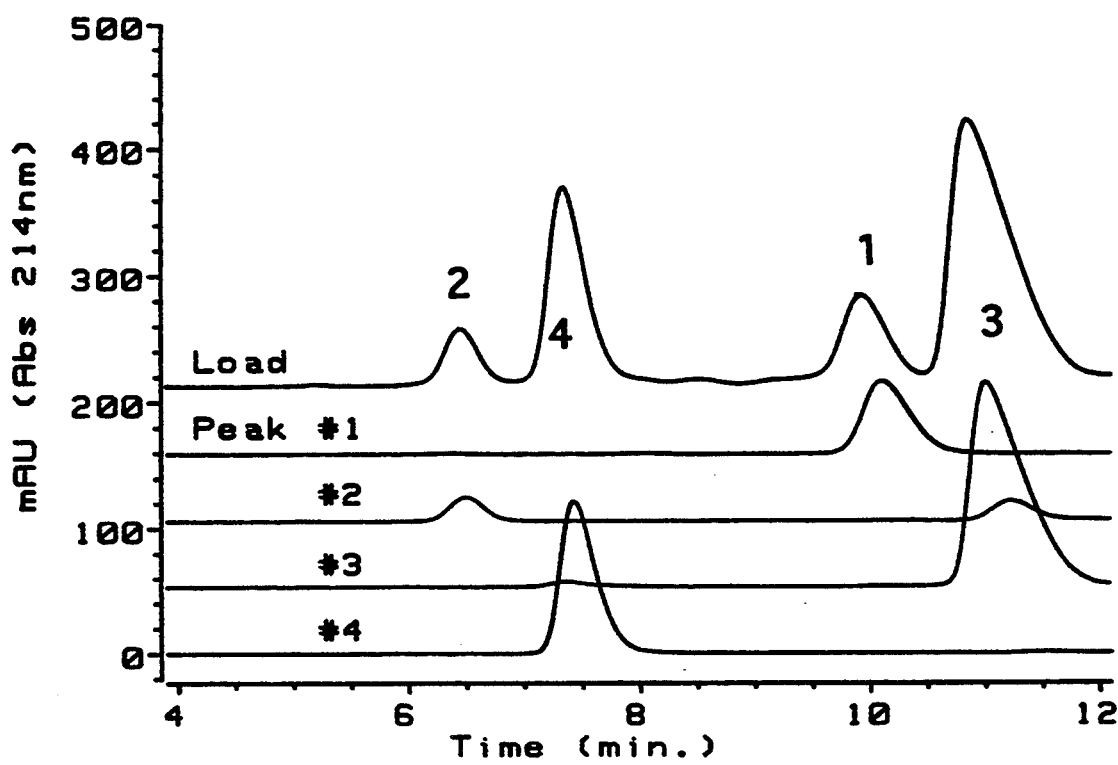
Figure 15A:
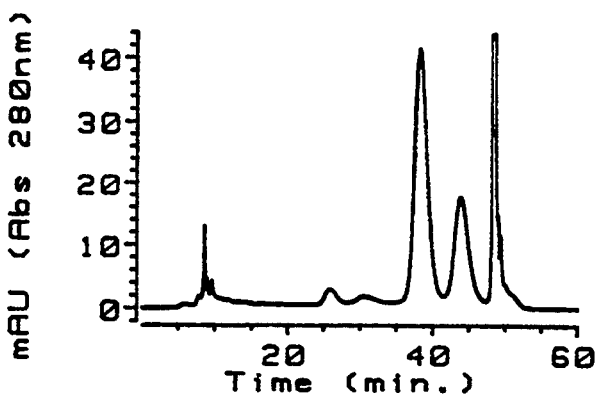
FIGS. 15A–H are a comparison of different preparative media, wherein the RP-HPLC chromatography in each case was performed on columns with similar geometry, using the 100 mM phosphate buffer, pH 7, mobile phase, 0.7 mL/minute, 50° C. The load level was maintained at 1000 μg rhIGF-I/mL bed volume.
Figure 15B:
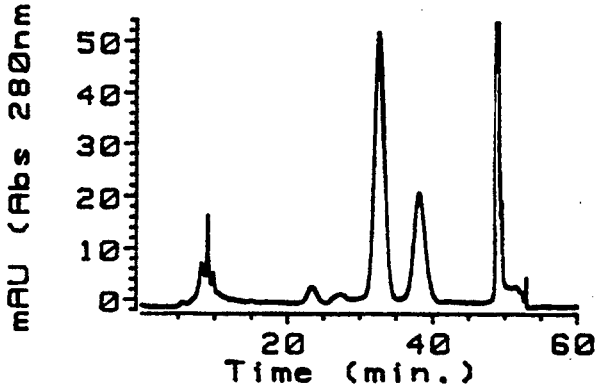
Figure 15C:
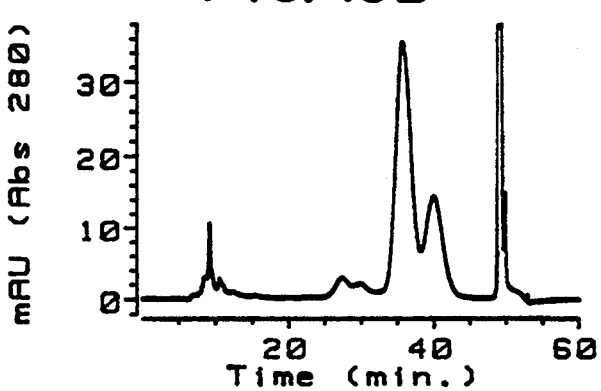
Figure 15D:
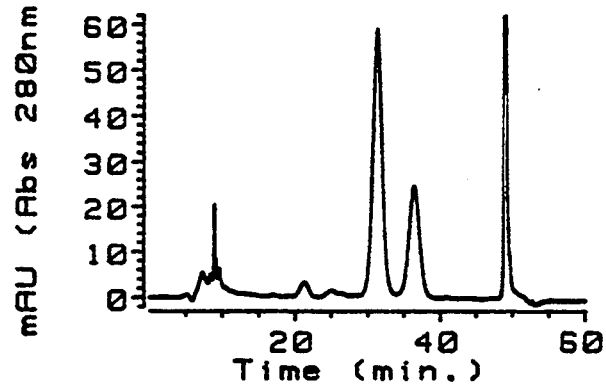
Figure 15E:
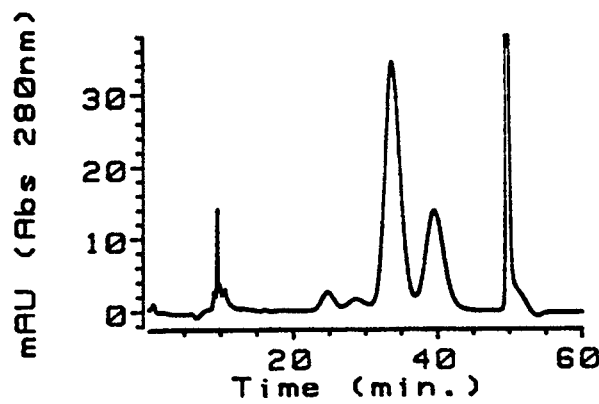
Figure 15F:
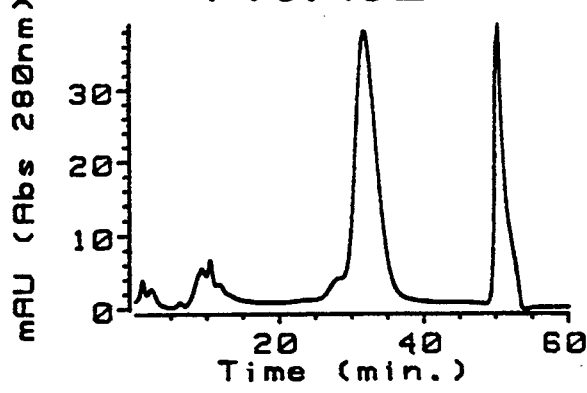
Figure 15G:
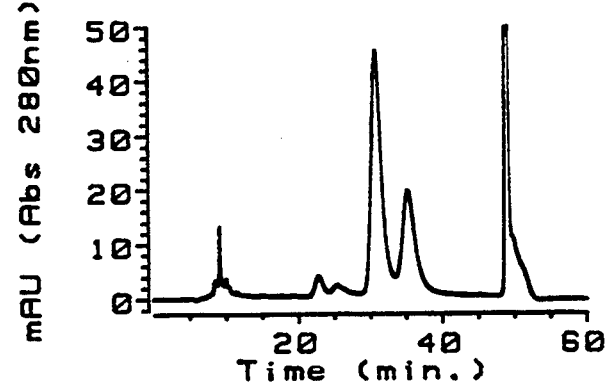
Figure 15H:
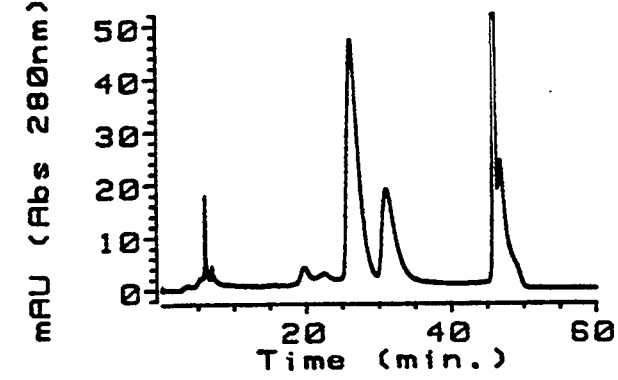

Four peak fractions were isolated from the preferred (100 mM phosphate/ACN, pH 7, 50° C.) Waters-C4 preparative chromatography conditions (FIG. 14A). Analysis on the Vydac-C18 column confirmed the relative mobility of the rhIGF-I variants. (FIG. 14B). A fifth variant that was apparently co-migrating with the main rhIGF-I peak using the acetate buffer was now well resolved (peak #2 analysis) and was identified as containing a hydroxamate species [Canova-Davis et al., supra] and a des-gly species. By initially using the protein load level evaluated during the methods development and then increasing the load in subsequent runs by a factor of two, the preferred chromatography appears to have an effective capacity > 1000 μg rhIGF-I product/mL of bed-volume (FIG. 14C). This 100-fold enhancement in the effective capacity between the initial acetate and the preferred phosphate mobile phases is primarily due to the misfolded rhIGF-I peak shift and the 5-fold increase in the difference in relative retention times between rhIGF-I and the less hydrophobic variant species, and is especially pronounced during non-linear elution due to mass overloading.

Additional analytical-size columns packed with a variety of preparative RP-HPLC media from other suppliers were evaluated using the 100 mM phosphate buffer, pH 7, ACN mobile phase (FIG. 15A-H). The conditions were adjusted as necessary for each individual column to have the product elute within a similar gradient slope (1% ACN gradient per 40 minutes). Chromatography on the various media resulted in similar profiles, independent of base matrix (silica or polymer), alkyl chain length (C4 or C8), or pore diameter (200–300 Å). Differences in particle size (7–20 μm) and pore diameter can significantly alter surface area and appear to affect resolution. The Amicon medium was unable to resolve the different variants under these conditions, although it was not independently evaluated to improve the separation.

The preferred preparative chromatography was scaled in two stages. The Hewlett-Packard 1090 HPLC system used for methods development delivers precise solvent blending by utilizing separate dual-syringe metering pumps for each reservoir to determine composition and flow, and is accurate even when using neat aqueous and organic phases. When neat solvents were tested with either the pilot-scale Waters DeltaPrep or preparative scale Biotage KiloPrep instruments, neither one had the absolute accuracy to deliver the 1% gradient needed for the separation. These chromatographs use low-pressure mixing with solenoid-based gradient formation. This problem was overcome by premixing the 100-mM phosphate buffer with 20% (A buffer) and 40% ACN (B buffer). In addition, these premixed buffers required no further degassing to prevent cavitation. The Waters RCM and cartridge format of column scale-up was chosen for its ability to utilize economically the same column hardware for different products, in addition to the radial compression technology, per se. Of the columns tested, the Waters-C4, 15-μm, 300-Å medium appeared to have comparable resolution and was readily available in the cartridge format. A counter-current heat exchanger and recirculating water bath was placed in-line with the column and the temperature of the column inlet and outlet monitored with thermocouples to maintain a 50° C. mobile phase throughout the separation.

The first scale increase from the Hewlett-Packard 1090 to the Waters Delta-Prep System involved a 145-fold increase in cross-sectional area at constant column length, from the analytical size 0.39×30 cm (3.58 mL bed-volume) stainless steel column to a 4.7×30 cm (520 mL) radial compression cartridge. Use of the same gradient slope of 1% ACN over 40 minutes and maintenance of the residence time at approximately 5 minutes (5.76 cm/minute) increased the flow rate to 100 mL/minute with identical chromatography. A sequence of cycles was initiated by running a single blank through the system to fully equilibrate the column from room temperature to 50° C. (as measured at the column outlet) with a 1° C. temperature drop across the column.

The second scale increase from the Waters DeltaPrep to the Biotage KiloPrep System was accomplished in both column dimensions. The cross-sectional area was increased 4.5-fold and the length 2-fold to a 10×60 cm (4.71 L) cartridge for an additional nine-fold scale-up, or an overall total of 1305-fold scale-up relative to the analytical column. Since the bed geometry had changed, the flow rate was adjusted based on a linear velocity to 450 mL/minute, using a proportionately larger heat-exchanger. The cycle time was increased to account for the slower flow rate, maintaining the same relative gradient volume. The chromatogram was similar to those from the analytical and pilot-scale runs. The purity of the collected product peak was >99% rhIGF-I, as assessed by the Vydac-C18 analysis. At load levels of 1000 μg rhIGF-I/mL of bed volume, 4.5 g of product can be processed per cycle in the large RCM. The chromatography using the ProChrom axial compression system packed with bulk 15-μm Waters-C4 media was comparable. The mass balance of product across the column at the various scales was identical. See Table 2.

TABLE 2
Recovery of IGF-I during RP-HPLC Scale-up

| Column | Dimensions (cm) | Bed Volume | Scale-up | Purity | Recovery Mass | Percent |
|---|---|---|---|---|---|---|
| Analytical | 0.39 × 30 | 3.58 mL | 1-fold | >99% | 3.5 mg | 97 |
| Pilot RCM | 4.7 × 30 | 520 mL | 145-fold | >99% | 0.5 g | 96 |
| Prep RCM | 10 × 60 | 4.71 L | 1305-fold | >99% | 4.5 g | 96 |

EXAMPLE IV

In this example properly folded and misfolded proteins are separated using hydrophobic interaction chromatography (HIC). The procedure is shown to be applicable to both IGF-I and brain IGF-I.

A. Introduction

During in vitro protein folding, some protein may not refold to its native three-dimensional structure but rather to other structures which differ with respect to their stability, solubility, immunogenicity, or bioactivity. These misfolded variants must be removed during recovery to avoid undesirable side-effects such as antigenicity or loss of potency. If the misfolded species is insoluble it may be easily removed by solid/liquid separation techniques such as centrifugation and filtration. On the other hand, if the misfolded variants are soluble, higher resolution adsorption techniques such as chromatography will be required to remove them.

When produced in prokaryotic cells or when refolded in vitro, IGF-I forms a soluble stable misfolded variant. Misfolded IGF-I has an altered disulfide pairing pattern and three-dimensional structure relative to native IGF-I and lacks native pharmacological activity. The difference in three-dimensional structure between the misfolded and correctly folded IGF-I could give rise to an antigenic response to one or both forms, precluding the therapeutic use of IGF-I.

HIC involves sequential adsorption and desorption of protein from solid matrices mediated through noncovalent hydrophobic bonding. The strength of the association between a protein and a matrix depends on several factors, including the size and hydrophobic character of the immobilized functional group, the polarity and surface tension of the surrounding solvent, and the hydrophobicity of the protein. The binding capacity of HIC matrices tends to be low due to the need for the immobilized hydrophobic ligand to be widely spaced. Further, the capacity of a medium for a given protein varies inversely with the level of hydrophobic impurities in the sample preparation. In order to resolve a desired protein from variants and other impurities while simultaneously maximizing capacity, it is necessary to identify a suitable HIC solid-phase medium as well as suitable mobile phases for load, wash, and elution.

B. Stationary Phase Media

The most suitable media for separating correctly folded and misfolded IGF-I were those having immobilized phenyl functional groups. Phenyl-based HIC media from different vendors exhibited different efficiency for resolving these IGF-I forms. Best results were achieved with Phenyl Toyopearl media by Toso-Haas. Similar results were obtained using Phenyl SEPHAROSE TM agarose CL4B from Pharmacia.

Other HIC-immobilized functional groups facilitated separation of correctly folded and misfolded IGF-I. Examples were octyl groups, such as those on Octyl SEPHAROSE TM agarose CL4B media from Pharmacia, and propyl groups, such as those on High Propyl media from Baker. Other HIC functional groups which were tested and found to be suitable, but less effective, under these conditions included the alkoxy, butyl, and isoamyl moieties.

C. Mobile Phase Composition

A variety of mobile phase conditions can be used to wash and differentially elute IGF-I forms from suitable chromatographic media. These mobile phases can contain several different chemical species that influence the association between IGF-I and the stationary phase in different ways. Consequently, the best concentration for a given species depended on the types and concentrations of other chemical species present in solution.

Correctly folded and misfolded IGF-I can be resolved on an HIC column by decreasing gradients or steps of mobile-phase ammonium sulfate {$(NH_4)_2SO_4$} concentration. Both IGF-I forms bound to the column when loaded in solutions containing 1M $(NH_4)_2SO_4$. Ammonium sulfate influences the binding of IGF-I to the stationary media by modulating the surface tension of the mobile phase. Other agents that similarly affected surface tension, such as sodium chloride, sodium citrate, and tetramethyl ammonium chloride, were also applicable.

Correctly folded and misfolded IGF-I can also be resolved during column chromatography by eluting bound protein with increasing gradients or steps in concentration of relatively polar organic solvents. Examples of suitable solvents include ethanol (EtOH), ACN, and acetic acid. Both forms of IGF-I bound to the stationary phase when loaded from solutions containing appropriate levels of $(NH_4)_2SO_4$, typically 1M, and low concentrations of relatively apolar solvent, such as less than 5% (v/v) EtOH. Correctly folded and misfolded IGF-I differentially eluted when exposed to a mobile phase containing a constant $(NH_4)_2SO_4$ concentration, such as between 0.3 and 0.7M, and an increasing concentration of relatively apolar solvent, such as between 5% and 20% (v/v) EtOH.

The strength of the association between IGF-I forms and HIC media depended on the mobile-phase pH. IGF-I forms bound more tightly to HIC media under acidic conditions, near pH 3, than under neutral conditions, near pH 7. Thus, IGF-I eluted from HIC columns at higher $(NH_4)_2SO_4$ concentration (or lower EtOH concentration) at pH 7 than at pH 3. The relative hydrophobicity of correctly folded and misfolded IGF-I also depended on solution pH. Thus, correctly folded and misfolded IGF-I could be resolved by an increasing gradient or steps in pH, such as between pH 3 and pH 7, at low $(NH_4)_2SO_4$ concentration, such as less than 0.1M.

Separation of correctly folded from misfolded IGF-I could also be obtained by simultaneously varying several properties of the mobile phase during gradient or step elution. For instance, use of a mobile phase that simultaneously varied in $(NH_4)_2SO_4$ concentration, apolar solvent concentration, and pH during elution provided resolution as good as or better than a mobile phase which only varied in $(NH_4)_2SO_4$ concentration during elution. ps D. Protein Hydrophobicity Brain IGF-I is a naturally truncated form of IGF-I lacking the first three N-terminal residues present on the IGF-I molecule. Brain IGF-I also produces a misfolded species when produced in prokaryotic cells. The correctly folded and misfolded forms of brain IGF-I can be separated by HIC. Brain IGF-I binds more tightly to HIC media than does full-length IGF-I, but this does not hinder the use of HIC for separating the correctly folded and misfolded brain IGF-I forms. For example, both forms of brain IGF-I bound to phenyl Toyopearl media when loaded from a pool containing 0.25M NaCl, 10 mM acetic acid (HOAc), at pH 5. Misfolded brain IGF-I eluted during a wash with 0.25M NaCl, 20 mM phosphate, at pH 7. Correctly folded brain IGF-I eluted with 20 mM HOAc, pH 3.2.

E. Examples

A solution of IGF-I obtained from the S-SEPHAROSE TM agarose purification steps of Examples I and II in 0.2M citrate, pH 6, was adjusted to pH 3.0 with phosphoric acid. The solution was then conditioned by the addition of 3.5M ammonium sulfate to a final concentration of 0.4M. This solution was then applied to a column of phenyl Toyopearl 650M equilibrated in 0.4M ammonium sulfate, 50 mM acetate, pH 3.0. After the load, the column was washed with 0.5 CV of equilibration buffer. The column was then washed with 2.0 CV of 0.1M ammonium sulfate, 50 mM acetate, pH 3. The correctly folded IGF-I was then eluted with 50 mM acetate, pH 4.0.

In another experiment, a column was equilibrated, loaded, and washed as described in the first experiment of this example. The correctly folded IGF-I was then eluted with a linear gradient over two CV from 0.1M ammonium sulfate, 50 mM acetate, pH 3, to 50 mM citrate/50 mM phosphate, pH 6.8.

In a third experiment, a solution of IGF-I obtained from the cation-exchange purification step of Example II was conditioned by the addition of 3.5M ammonium sulfate to a final concentration of 1M. This solution was then applied to a column of phenyl Toyopearl 650M equilibrated in 1M ammonium sulfate, 100 mM phosphate, pH 7.0. After the load, the column was washed with 1 CV of equilibration buffer. The column was then washed with 2.0 CV of 0.7M ammonium sulfate, 100 mM phosphate, pH 7.0. The correctly folded IGF-I was then eluted with 0.4M ammonium sulfate, 100 mM phosphate, pH 7.0.

EXAMPLE V

In this example, the HIC pool from Example IV is purified on a RP-HPLC using the preferred phosphate mobile phase described in Example III.

The HIC pool is devoid of the misfolded and oxidized-misfolded rhIGF-I variants. Since these two variants constitute approximately 30% of the total IGF-I present in the S-SEPHAROSE TM agarose pool, removal of these species prior to RP-HPLC improves the capacity of this step approximately 20 fold.

ACN was added to the HIC pool to a final concentration of 20% (v/v). After pH adjustment to 7, the conditioned HIC pool was loaded on to a C-4 RP-HPLC column previously equilibrated with 20% ACN in 0.1M phosphate, pH 7. The column was washed with equilibration buffer and the IGF-I was eluted with a linear gradient of approximately 24–25% ACN in 0.1M phosphate, pH 7. The duration of the gradient was approximately 9 CV. After the IGF-I was eluted, the column was regenerated with 1 CV of 40% ACN in 0.1M phosphate, pH 7, prior to re-equilibration.

EXAMPLE VI

In this example, the RP-HPLC pool is purified on a cation-exchange resin.

The HPLC pool from Example III or V was titrated to pH 3.5 by the addition of 1N HCl. The adjusted pool was loaded to a cation-exchange resin, in this case an S-SEPHAROSE TM agarose Fast Flow TM (Pharmacia) column, previously equilibrated with 50 mM acetic acid, 50 mM NaCl, pH 3.5. After loading, the column was washed with 2 CV of equilibration buffer, 4 CV each of 50 mM Tris, pH 8, and 10 mM citrate, pH 6, to remove impurities and contaminants. The bound IGF-I was eluted with 0.2M citrate, pH 6. After elution, the column was regenerated with 0.5N NaOH.

---

What is claimed is:

1. A process for purifying IGF-I comprising loading a mixture containing IGF-I onto a preparative reversed-phase liquid chromatography column and eluting the IGF-I from the column with a buffer at a pH of about 6–8 containing an alcoholic or polar aprotic solvent at a concentration of about 20–30% (v/v).

2. The process of claim 1 wherein the column is packed with a medium having a particle diameter of about 5–40 μm, a pore size of about 100–4000 Å, and a C4, C8, or C18 alkyl group.

3. The process of claim 1 wherein the medium has a particle diameter of about 10–15 μm and a pore size of about 150–300 Å, and is a C4 silica medium.

4. The process of claim 1 wherein the mixture is loaded in about 5–20% (v/v) of an alcoholic or polar aprotic solvent.

5. The process of claim 1 wherein the level of IGF-I loaded is about 0.02 to 30 mg IGF-I/mL bed volume.

6. The process of claim 1 wherein sodium chloride or potassium chloride is also present in the buffer at a concentration of from about 10 mM to the solubility limit of the sodium chloride or potassium chloride.

7. The process of claim 1 wherein the buffer is a phosphate buffer in which the phosphate is at a concentration from about 10 mM to the solubility limit of the phosphate.

8. The process of claim 7 wherein the phosphate buffer is at a concentration of about 10–200 mM.

9. The process of claim 7 wherein the phosphate buffer is about 100 mM sodium or potassium phosphate, pH adjusted to about 7.

10. The process of claim 1 wherein the solvent is acetonitrile.

11. The process of claim 1 further comprising loading the IGF-I-containing eluate onto a cation-exchange column and eluting the IGF-I.

12. The process of claim 11 wherein the IGF-I-containing eluate from the cation-exchange column is desalted and diafiltered or gel filtered.

13. An IGF-I composition prepared by the process of claim 12 comprising a pharmaceutically acceptable carrier.

14. A process for purifying IGF-I comprising:
(a) loading a buffer containing IGF-I at a pH of about 3–8 onto a hydrophobic interaction chromatography column;
(b) washing the column with a buffer at a pH of about 3–8;
(c) eluting the IGF-I with a buffer at a pH of about 3–8;
(d) loading the IGF-I-containing eluant onto a preparative reversed-phase liquid chromatography column; and
(e) eluting the IGF-I from the reversed-phase liquid chromatography column with a buffer at a pH of about 6–8 containing an alcoholic or polar aprotic solvent at a concentration of about 20–30% (v/v).

15. The process of claim 14 wherein the hydrophobic interaction chromatography column is a phenyl column.

16. The process of claim 14 wherein the pH of the buffer in steps (a) to (c) is about 3-4.

17. The process of claim 14 wherein the buffers for steps (a)-(c) are a citrate or ammonium buffer or both at pH about 6-8.

18. The process of claim 17 wherein the buffers for steps (a)-(c) are 0.1-1 mM ammonium sulfate or ammonium citrate.

19. The process of claim 14 wherein the buffer for step (e) is a phosphate buffer consisting of about 100 mM sodium or potassium phosphate, pH adjusted to about 7 and the solvent for step (e) is acetonitrile.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
( A ) LENGTH: 485 bases
( B ) TYPE: nucleic acid
( C ) STRANDEDNESS: single
( D ) TOPOLOGY: linear ( x i ) SEQUENCE DESCRIPTION: SEQ ID NO:1:

```
GAATTCATGA GATTTCCTTC AATTTTTACT GCAGTTTTAT TCGCAGCATC                50

CTCCGCATTA GCTGCTCCAG TCAACACTAC AACAGAAGAT GAAACGGCAC               100
```

```
AAATTCCGGC TGAAGCTGTC ATCGGTTACT TAGATTTAGA AGGGGATTTC          150

GATGTTGCTG TTTTGCCATT TTCCAACAGC ACAAATAACG GGTTATTGTT          200

TATAAATACT ACTATTGCCA GCATTGCTGC TAAAGAAGAA GGGGTATCTT          250

TGGATAAAAG AGGTCCGGAA ACTCTGTGCG GCGCTGAGCT GGTTGACGCT          300

CTGCAGTTCG TATGTGGTGA TCGAGGCTTC TACTTCAACA AACCGACTGG          350

GTACGGATCC TCCTCTCGTC GTGCTCCGCA AACCGGCATC GTTGATGAAT          400

GCTGTTTTCG GTCCTGTGAC CTTCGCCGTC TGGAAATGTA CTGCGCTCCG          450

CTGAAACCGG CTAAGTCTGC ATAGTCGACG AATTC                          485
```

( 2 ) INFORMATION FOR SEQ ID NO:2:

( i ) SEQUENCE CHARACTERISTICS:
        ( A ) LENGTH: 30 bases
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
CATGGCCGGT CCGGAAACTC TGTGCGGCGC                                30
```

( 2 ) INFORMATION FOR SEQ ID NO:3:

( i ) SEQUENCE CHARACTERISTICS:
        ( A ) LENGTH: 22 bases
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CGGCCAGGCC TTTGAGACAC GC                                        22
```

( 2 ) INFORMATION FOR SEQ ID NO:4:

( i ) SEQUENCE CHARACTERISTICS:
        ( A ) LENGTH: 51 bases
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
CATGGCCGGT CCCGAAACTC TGTGCGGTGC TGAACTGGTT GACGCTCTGC          50

A                                                               51
```

( 2 ) INFORMATION FOR SEQ ID NO:5:

( i ) SEQUENCE CHARACTERISTICS:
        ( A ) LENGTH: 43 bases
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
CGGCCAGGGC TTTGAGACAC GCCACGACTT GACCAACTGC GAG                 43
```

( 2 ) INFORMATION FOR SEQ ID NO:6:

( i ) SEQUENCE CHARACTERISTICS:
        ( A ) LENGTH: 18 bases
        ( B ) TYPE: nucleic acid
        ( C ) STRANDEDNESS: single
        ( D ) TOPOLOGY: linear ( x i ) SEQUENCE DESCRIPTION: SEQ ID NO:6:

CATGGCCTCC CCATATTC 18

( 2 ) INFORMATION FOR SEQ ID NO:7:

( i ) SEQUENCE CHARACTERISTICS:
( A ) LENGTH: 18 bases
( B ) TYPE: nucleic acid
( C ) STRANDEDNESS: single
( D ) TOPOLOGY: linear ( x i ) SEQUENCE DESCRIPTION: SEQ ID NO:7:

CGGAGGGGTA TAAGGAGC 18

( 2 ) INFORMATION FOR SEQ ID NO:8:

( i ) SEQUENCE CHARACTERISTICS:
( A ) LENGTH: 67 bases
( B ) TYPE: nucleic acid
( C ) STRANDEDNESS: single
( D ) TOPOLOGY: linear ( x i ) SEQUENCE DESCRIPTION: SEQ ID NO:8:

TCGTCGTGCT CCCCAGACTG GTATTGTTGA CGAATGCTGC TTTCGTTCTT 50

GCGACCTGCG TCGTCTG 67

( 2 ) INFORMATION FOR SEQ ID NO:9:

( i ) SEQUENCE CHARACTERISTICS:
( A ) LENGTH: 70 bases
( B ) TYPE: nucleic acid
( C ) STRANDEDNESS: single
( D ) TOPOLOGY: linear ( x i ) SEQUENCE DESCRIPTION: SEQ ID NO:9:

AGAACGCTGG ACGCAGCAGA CCTTTACATA ACGCGAGGGG ACTTTGGGCG 50

ATTTAGACGA ATCTTCGAGG 70